(12) United States Patent
Haff

(10) Patent No.: US 12,270,126 B2
(45) Date of Patent: Apr. 8, 2025

(54) WOUND DRESSING

(71) Applicant: University of Central Oklahoma, Edmond, OK (US)

(72) Inventor: Maurice Haff, Edmond, OK (US)

(73) Assignee: UNIVERSITY OF CENTRAL OKLAHOMA, Edmond, OK (US)

( * ) Notice: Subject to any disclaimer, the term of this patent is extended or adjusted under 35 U.S.C. 154(b) by 0 days.

(21) Appl. No.: 18/819,088

(22) Filed: Aug. 29, 2024

(65) Prior Publication Data

US 2024/0415764 A1 Dec. 19, 2024

Related U.S. Application Data

(63) Continuation of application No. 18/442,805, filed on Feb. 15, 2024, which is a continuation of application No. 17/553,539, filed on Dec. 16, 2021, now Pat. No. 11,913,139, which is a continuation of application No. 17/229,612, filed on Apr. 13, 2021, now Pat. No. 11,208,735, which is a continuation-in-part of application No. 16/909,077, filed on Jun. 23, 2020, now Pat. No. 10,995,425, which is a continuation-in-part of application No. 16/833,116, filed on Mar. 27, 2020, now Pat. No. 10,876,223, which is a continuation of application No. 16/460,589, filed on Jul. 2, 2019, now Pat. No. 10,640,888.

(51) Int. Cl.
| | |
|---|---|
| *A61L 15/16* | (2006.01) |
| *A61K 9/00* | (2006.01) |
| *A61K 45/06* | (2006.01) |
| *A61K 47/02* | (2006.01) |
| *A61K 47/10* | (2017.01) |
| *A61K 47/12* | (2006.01) |
| *A61K 47/14* | (2017.01) |
| *A61K 47/34* | (2017.01) |
| *A61K 47/38* | (2006.01) |
| *A61L 15/20* | (2006.01) |
| *A61L 15/38* | (2006.01) |
| *B01D 67/00* | (2006.01) |
| *B05B 5/053* | (2006.01) |
| *B05B 5/08* | (2006.01) |
| *B05B 5/14* | (2006.01) |
| *B05C 19/02* | (2006.01) |
| *B05D 3/02* | (2006.01) |
| *B32B 5/02* | (2006.01) |
| *B32B 5/12* | (2006.01) |
| *B32B 5/26* | (2006.01) |
| *D01D 5/00* | (2006.01) |
| *D04H 1/413* | (2012.01) |
| *D04H 3/02* | (2006.01) |

(52) U.S. Cl.
CPC ......... *D01D 5/0092* (2013.01); *A61K 9/0053* (2013.01); *A61K 45/06* (2013.01); *A61K 47/02* (2013.01); *A61K 47/10* (2013.01); *A61K 47/12* (2013.01); *A61K 47/14* (2013.01); *A61K 47/34* (2013.01); *A61K 47/38* (2013.01); *B01D 67/00042* (2022.08); *B05B 5/0536* (2013.01); *B05B 5/082* (2013.01); *B05B 5/14* (2013.01); *B05C 19/025* (2013.01); *B05D 3/0254* (2013.01); *B32B 5/12* (2013.01); *B32B 5/266* (2021.05); *D01D 5/0084* (2013.01); *D04H 1/413* (2013.01); *D04H 3/02* (2013.01); *B32B 2307/7163* (2013.01); *B32B 2535/00* (2013.01)

(58) Field of Classification Search
CPC ......... A61K 47/10; A61L 15/16; A61L 15/20; A61L 15/38; B32B 5/022; B32B 5/26
See application file for complete search history.

(56) References Cited

U.S. PATENT DOCUMENTS

| | | | |
|---|---|---|---|
| 1,975,504 A | 10/1934 | Formhals | |
| 4,043,331 A * | 8/1977 | Martin | D04H 1/56 264/441 |

(Continued)

FOREIGN PATENT DOCUMENTS

| | | |
|---|---|---|
| KR | 101224544 B1 | 1/2013 |
| KR | 101689740 B1 | 12/2016 |

OTHER PUBLICATIONS

Ataei et al., "Essential Oils-Loaded Electrospun Biopolymers: A Future Perspective for Active Food Packaging", Hindawi, Advances in Polymer Technology, vol. 2020, Article ID 9040535, 21 pages, https://doi.org/10.1155/2020/9040535.

(Continued)

*Primary Examiner* — Joanna Pleszczynska
(74) *Attorney, Agent, or Firm* — CALDERON SAFRAN & WRIGHT P.C.

(57) ABSTRACT

A method for controlling fiber cross-alignment in a nanofiber membrane, comprising: providing a multiple segment collector in an electrospinning device including a first and second segment electrically isolated from an intermediate segment positioned between the first and second segment, collectively presenting a cylindrical structure, rotating the cylindrical structure around a longitudinal axis proximate to an electrically charged fiber emitter; electrically grounding or charging edge conductors circumferentially resident on the first and second segment, maintaining intermediate collector electrically neutral; dispensing electrospun fiber toward the collector, the fiber attaching to edge conductors and spanning the separation space between edge conductors; attracting electrospun fiber attached to the edge conductors to the surface of the cylindrical structure, forming a first fiber layer; increasing or decreasing rotation speed of the cylindrical structure to alter the angular cross-alignment relationship between aligned nanofibers in adjacent layers, the rotation speed being altered to achieve a target relational angle.

20 Claims, 26 Drawing Sheets

(56) References Cited

U.S. PATENT DOCUMENTS

| | | | |
|---|---|---|---|
| 7,993,567 | B2 | 8/2011 | Scott-Carnell et al. |
| 8,852,621 | B2 | 10/2014 | Patel et al. |
| 9,359,694 | B2 | 6/2016 | Khandaker et al. |
| 9,809,906 | B2 | 11/2017 | Khandaker et al. |
| 10,041,189 | B2 | 8/2018 | Kocis et al. |
| 10,415,156 | B2 | 9/2019 | Khandaker et al. |
| 10,640,888 | B1 | 5/2020 | Haff |
| 10,876,223 | B1 | 12/2020 | Haff |
| 11,208,735 | B2 | 12/2021 | Haff |
| 11,913,139 | B2 | 2/2024 | Haff |
| 2006/0205646 | A1 | 9/2006 | Sanders |
| 2007/0269481 | A1 | 11/2007 | Li et al. |
| 2010/0112020 | A1 | 5/2010 | Westbroek et al. |
| 2010/0233115 | A1 | 9/2010 | Patel et al. |
| 2014/0141152 | A1 | 5/2014 | Sostek et al. |
| 2019/0338445 | A1 | 11/2019 | Haff et al. |
| 2021/0002789 | A1 | 1/2021 | Haff |
| 2024/0200230 | A1 | 6/2024 | Haff |

OTHER PUBLICATIONS

Choi JS, Lee SJ, Christ GJ, Atala A, Yoo JJ. "The influence of electrospun aligned poly(epsilon-caprolactone)/collagen nanofiber meshes on the formation of self-aligned skeletal muscle myotubes". Biomaterials. Jul. 2008; 29(19):2899-906.

Currie, S., Shariatzadeh, F. J., Singh, H., Logsetty, S & Liu, S. "Highly Sensitive Bacteria-Responsive Membranes Consisting of Core-Shell Polyurethane Polyvinylpyrrolidone Electrospun Nanofibers for In Situ Detection of Bacterial Infections". ACS Applied Materials & Interfaces. 2020 12 (41), 45859-45872. DOI: 10.1021/acsami.0c14213.

Hosseinpor, H., Khaledi, A. & Esmaeili, D. "The properties of nanofiber scaffolds of polyurethane-Cinnamomum zeylanicum against pathogens of Pseudomonas aeruginosa and *Staphylococcus aureus*". Polym. Bull. (2020). https://doi.org/10.1007/s00289-019-03095-1.

Hülya Kesici Güler, Funda Cengiz çallioglu & Emel Sesli çetin (2019), "Antibacterial PVP/cinnamon essential oil nanofibers by emulsion electrospinning", The Journal of The Textile Institute, 110:2, 302-310, DOI: 10.1080/00405000.2018.1477237.

Jianfeng Zhang, Dongzhi Yang, Ziping Zhang, and Jun Nie (2008). "Preparation of biaxial orientation mats from single fibers." Polym. Adv. Technol 2010, 21 606-608.

Li D, Xia Y. "Electrospinning of nanofibers: reinventing the wheel?", Adv Mater. 2004;16:1151-1170.

Mele, E. "Electrospinning of Essential Oils", Polymers 2020, 12(4), 908., https://doi.org/10.3390/polym12040908.

R. Frykberg, J. Banks (2015) "Challenges in the Treatment of Chronic Wounds" Advances in Wound Care, vol. 4, No. 9, 560-582.

Reneker, D. H., A. L. Yarin, H. Fong and S. Koombhongse (2000) "Bending instability of electrically charged liquid jets of polymer solutions in electrospinning." Journal of Applied physics 87(9): 4531-4547.

Ritu Jain, Saritha Shetty, Khushwant S. Yadav, "Unfolding the electrospinning potential of biopolymers for preparation of nanofibers", Journal of Drug Delivery Science and Technology, vol. 57, 2020, 101604, ISSN 1773-2247, https://doi.org/10.1016/j.jddst.2020.101604.

Unalan, I.; Endlein, S.J.; Slavik, B.; Buettner, A.; Goldmann, W.H.; Detsch, R.; Boccaccini, A.R. "Evaluation of Electrospun Poly(e-Caprolactone)/Gelatin Nanofiber Mats Containing Clove Essential Oil for Antibacterial Wound Dressing". Pharmaceutics 2019, 11, 570. https://doi.org/10.3390/pharmaceutics11110570.

Yarin, K Yarin, A. L., W. Kataphinan and D. H. Reneker (2005). "Branching in electrospinning of nanofibers." Journal of Applied Physics 98(6):—ataphinan et al. 2005.

Zahra Abdali, Sarvesh Logsetty, and Song Liu, "Bacteria-Responsive Single and Core-Shell Nanofibrous Membranes Based on Polycaprolactone/Poly(ethylene succinate) for On-Demand Release of Biocides", ACS Omega 2019 4 (2), 4063-4070.

\* cited by examiner

WOUND DRESSING

CROSS REFERENCE TO RELATED APPLICATION

This application is a continuation and claims benefit of U.S. patent application Ser. No. 18/442,805 filed on Feb. 15, 2024 by the University of Central Oklahoma (Applicant), entitled "Radially cross-aligned nanofiber membrane" the entire disclosure of which is incorporated herein by reference in its entirety for all purposes, and which application is a continuation and claims benefit of U.S. patent application Ser. No. 17/553,539 filed on Dec. 16, 2021 by the University of Central Oklahoma (Applicant), entitled "Radially cross-aligned nanofiber membrane" the entire disclosure of which is incorporated herein by reference in its entirety for all purposes, and which application is a continuation and claims benefit of U.S. patent application Ser. No. 17/229,612 filed on Apr. 13, 2021 by the University of Central Oklahoma (Applicant), entitled "Method and apparatus for controlling fiber cross-alignment in a nanofiber membrane" the entire disclosure of which is incorporated herein by reference in its entirety for all purposes, and which application is a continuation-in-part and claims benefit of U.S. patent application Ser. No. 16/909,077 filed on Jun. 23, 2020, now U.S. Pat. No. 10,995,425 by the University of Central Oklahoma (Applicant), entitled "Method and apparatus for fabricating a multifunction fiber membrane" the entire disclosure of which is incorporated herein by reference in its entirety for all purposes, and which application is a continuation-in-part and claims benefit of U.S. patent application Ser. No. 16/833,116 filed on Mar. 27, 2020, now U.S. Pat. No. 10,876,223 by the University of Central Oklahoma (Applicant), entitled "Method and apparatus for accumulating cross-aligned fiber in an electrospinning device" the entire disclosure of which is incorporated herein by reference in its entirety for all purposes, and which application is a continuation and claims benefit of U.S. patent application Ser. No. 16/460,589 filed on Jul. 2, 2019, now U.S. Pat. No. 10,640,888 by the University of Central Oklahoma (Applicant) in the name of Maurice Haff, entitled "Method and apparatus for accumulating cross-aligned fiber in an electrospinning device" the entire disclosure of which is incorporated herein by reference in its entirety for all purposes.

STATEMENT AS TO RIGHTS TO INVENTIONS MADE UNDER FEDERALLY SPONSORED RESEARCH OR DEVELOPMENT

This invention was made without government support.

FIELD OF THE INVENTION

The present invention generally relates to the field of electrospinning. More specifically, the invention relates to the controlled accumulation of cross-aligned fibers of micron to nano size diameters on a collector to produce layered structures in various dimensions from an electrospin process.

All of the, patents, patent applications, and non-patent literature that are referred to herein are incorporated by reference in their entirety as if they had each been set forth herein in full. Note that this application is one in a series of applications by the Applicant covering methods and apparatus for enabling biomedical applications of nanofibers. The term "fiber" and the term "nanofiber" may be used interchangeably, and neither term is limiting. The disclosure herein goes beyond that needed to support the claims of the particular invention set forth herein. This is not to be construed that the inventor is thereby releasing the unclaimed disclosure and subject matter into the public domain. Rather, it is intended that patent applications will be filed to cover all of the subject matter disclosed below. Also, please note that the terms frequently used below "the invention" or "this invention" is not meant to be construed that there is only one invention being discussed. Instead, when the terms "the invention" or "this invention" are used, it is referring to the particular invention being discussed in the paragraph where the term is used.

BACKGROUND OF THE INVENTION

The basic concept of electrostatic spinning (or electrospinning) a polymer to form extremely small diameter fibers was first patented by Anton Formhals (U.S. Pat. No. 1,975,504). Electrostatically spun fibers and nonwoven webs formed therefrom have traditionally found use in filtration applications, but have begun to gain attention in other industries, including in nonwoven textile applications as barrier fabrics, wipes, medical and pharmaceutical uses, and the like.

Electrospining is a process by which electrostatic polymer fibers with micron to nanometer size diameters can be deposited on a substrate such as a flat plate. By way example, Westbroek, et el (US20100112020) illustrate deposition of electrospun fibers on a flat plate as shown in FIG. 1. Such fibers have a high surface area to volume ratio, which can improve the structural and functional properties of a fiber structure collected on a substrate. Typically, a jet of polymer solution is driven from a highly positive charged metallic needle (i.e. an emitter) to the substrate which is typically grounded. Sessile and pendant droplets of polymer solutions may then acquire stable shapes when they are electrically charged by applying an electrical potential difference between the droplet and the flat plate. These stable shapes result only from equilibrium of the electric forces and surface tension in the cases of inviscid, Newtonian, and viscoelastic liquids. In liquids with a nonrelaxing elastic force, that force also affects the shapes. When a critical potential has been reached and any further increase will destroy the equilibrium, the liquid body acquires a conical shape referred to as the Taylor cone.

Organic and synthetic polymers including but not limited to collagen, gelatin, chitosan, poly (lactic acid) (PLA), poly(glycolic acid) (PGA), and poly(lactide-co-glycolide) (PLGA) have been used for electrospinning. In addition to the chemical structure of the polymer, many parameters such as solution properties (e.g., viscosity, conductivity, surface tension, polymer molecular weight, dipole moment, and dielectric constant), process variables (e.g., flow rate, electric field strength, distance between a fiber emitter [e.g., needle] and collector [e.g., flat plate, drum], emitter tip design, and collector geometry), and ambient conditions (e.g., temperature, humidity, and air velocity) can be manipulated to produce fibers with desired composition, shape, size, and thickness. Polymer solution viscosity and collector geometry are important factors determining the size and morphology of electrospun fibers. Below a critical solution viscosity, the accelerating jet from the tip of the capillary breaks into droplets as a result of surface tension. Above a critical viscosity, the repulsive force resulting from the induced charge distribution on the droplet overcomes the surface tension, the accelerating jet does not break up, and results in collection of fibers on the grounded target. A variety of target types have been used, with flat plate and drum targets being common. By way of example, Korean Patent KR101689740B1 illustrates use of a drum target in electrospinning as shown in FIG. 2. Although the fiber shown in FIG. 2 appears as a single thread, the jet of fiber divides into many branches on its surface after the jet leaves the tip of the needle (Yarin, K Yarin, A. L., W. Kataphinan and D. H. Reneker (2005). "Branching in electrospinning of nanofibers." *Journal of Applied Physics* 98(6): —ataphinan et al. 2005). If not controlled, the branches of the fibers create a non-uniform deposition on the target collector. One objective of the present invention is to enable a more controlled deposition of fibers to achieve a more uniform and cross-aligned distribution of the fiber on a collector.

Many engineering applications require uniform distribution of the fiber on the substrate. For example, one of the most important cell morphologies associated with tissue engineering is elongated unidirectional cell alignment. Many tissues such as nerve, skeletal and cardiac muscle, tendon, ligament, and blood vessels contain cells oriented in a highly aligned arrangement, thus it is desirable that scaffolds designed for these tissue types are able to induce aligned cell arrangements. It is well documented that cells adopt a linear orientation on aligned substrates such as grooves and fibers. Aligned nanofiber arrays can be fabricated using the electrospinning method [Li D, Xia Y. Electrospinning of nanofibers: reinventing the wheel? Adv Mater. 2004; 16:1151-1170] and many studies have shown that cells align with the direction of the fibers in these scaffolds. It is known that electrospun fibers can be aligned by attracting the fibers to a pair of electrically grounded, opposing and rotating disks or a pair of electrically grounded, parallel wires. It is known that cross-alignment of fibers can be achieved by first attracting fibers between parallel collectors such as rotating disks or parallel wires, then harvesting those fibers on a substrate, rotating the substrate 90 degrees and then harvesting more fibers to produce cross-aligned fiber layers. By way of example, Khandaker, et al. in U.S. Pat. No. 9,359,694 illustrate use of opposing disks in fiber collection as shown in FIG. 3A. Further, Khandaker, et al. in U.S. Pat. No. 9,809,906 illustrate use of parallel wires in fiber collection as shown in FIG. 3B. Cross alignment of fibers in layers can also be achieved as reported by Zhang, et al where biaxial orientation mats were electrospun using a collector consisting of two rotating disks with conductive edge to collect fibers in one orientation, and an auxiliary electrode to induce an electrostatic field to force the fibers to align in another orientation. (Jianfeng Zhang, Dongzhi Yang, Ziping Zhang, and Jun Nie (2008). "Preparation of biaxial orientation mats from single fibers." Polym. Adv. Technol 2010, 21 606-608.) The biaxial orientation structure was formed with variation of rotation speed for each layer, without revolving the fiber mat during the electrospinning process. However, the degree of biaxial orientation was found to be strongly dependent on the rotation speed of the disks. A significant deficiency in the method was reported to be the destruction of a first fiber layer while forming a second cross-aligned fiber layer. This appears to be a limiting factor in fabricating larger size mats because the fibers in the first layer cannot withstand the forces imparted by higher rotation speeds needed to apply the second layer. Parallel collector plates have also been used, and may be combined with manual or robotic harvesting of fibers. By way of example, Korean Patent KR101224544B1 illustrates the use of parallel plates in fiber collection as shown in FIG. 4. Opposing disks, and both parallel wires and plates may be used to achieve fiber alignment and cross-alignment, but these known methods all suffer significant challenges in scalability for commercial applications, particularly as the physical dimensions of width and length of the desired mat are increased.

In addition to the influence on fiber arrangement, cell alignment can have positive effects on cell growth within tissue engineering scaffolds. Myotubes formed on aligned nanofiber scaffolds were more than twice the length of myotubes grown on randomly oriented fibers ($p<0.05$) and neurites extending from DRG explants on highly aligned scaffolds were 16 and 20% longer than those grown on intermediate and randomly aligned scaffolds respectively [Choi J S, Lee S J, Christ G J, Atala A, Yoo J J. The influence of electrospun aligned poly(epsilon-caprolactone)/collagen nanofiber meshes on the formation of self-aligned skeletal muscle myotubes. Biomaterials. 2008 July; 29(19):2899-906].

Growth of electrical bending instability (also known as whipping instability) and further elongation of the jet may be accompanied with the jet branching and/or splitting. Branching of the jet of polymer during the electrospin process has been observed for many polymers, for example, polycaprolactone (PCL)(Yarin, Kataphinan et al. 2005), polyethylene oxide (Reneker, D. H., A. L. Yarin, H. Fong and S. Koombhongse (2000) "Bending instability of electrically charged liquid jets of polymer solutions in electrospinning." *Journal of Applied physics* 87(9): 4531-4547). Such branching produces non-uniform deposition of fiber on a collector during the electrospin process.

Chronic wound care consumes a massive share of total healthcare spending globally. Care for chronic wounds has been reported to cost 2% to 3% of the healthcare budgets in developed countries (R. Frykberg, J. Banks (2015) "Challenges in the Treatment of Chronic Wounds" Advances in Wound Care, Vol. 4, Number 9, 560-582). In the United States, chronic wounds impact nearly 15% of Medicare beneficiaries at an estimated annual cost of $28 billion. In Canada, the estimated cost to the health system is $3.9 billion. Despite significant progress over the past decade in dealing with chronic (non-healing) wounds, the problem remains a significant challenge for healthcare providers and continues to worsen each year given the demographics of an aging population. Persistent chronic pain associated with chronic wounds is caused by tissue or nerve damage and is influenced by dressing changes and chronic inflammation at the wound site. Chronic wounds take a long time to heal and patients can suffer from chronic wounds for many years. Wound dressings are often extremely painful to remove, particularly for severe burn wounds. The removal of these dressings can peel away the fresh and fragile skin that is making contact with the dressing, causing extreme pain and prolonged recovery time. There is also a greater risk for infection and the onset of sepsis, which is can be fatal.

Research at the University of Manitoba has demonstrated positive effects of antimicrobial nanofiber membranes in treating the conditions of infection in chronic wounds (Zahra Abdali, Sarvesh Logsetty, and Song Liu, Bacteria-Responsive Single and Core-Shell Nanofibrous Membranes Based on Polycaprolactone/Poly(ethylene succinate) for On-Demand Release of Biocides, *ACS Omega* 2019 4 (2), 4063-4070). Subsequent research demonstrated a method of increasing the sensitivity response of polymeric core-shell nanofibers to lipase secreted by clinically relevant bacterial strains (Sarah Currie, Farinaz Jonidi Shariatzadeh, Hardev Singh, Sarvesh Logsetty, and Song Liu, Highly Sensitive Bacteria-Responsive Membranes Consisting of Core-Shell Polyurethane Polyvinylpyrrolidone Electrospun Nanofibers for In Situ Detection of Bacterial Infections, *ACS Applied Materials & Interfaces* 2020 12 (41), 45859-45872 DOI: 10.1021/acsami.0c14213). A PHA based core-shell structural nanofibrous mat incorporating a broad-spectrum potent biocide in the core of the nanofibers was fabricated by coaxial electrospinning. The nanofiborous mats produced comprised randomly oriented PHA based core-shell nanofibers. The random structure of the fibers limited surface contact with a wound and any resulting triggered release of biocides present in the outer layers of the mat. Further, the random orientation of the nanofibers presented less than optimal porosity for cell migration and exudate flow from a wound. In subsequent research, the sensitivity of an electrospun nanofibrous mat was increased by substituting polyurethane for PHA. A hemicyanine dye was incorporated to form a chromogenic probe with a labile ester linkage that can be enzymatically cleaved by bacterial lipase released from clinically relevant strains such as *Pseudomonas aeruginosa* and methicillin-resistant *Staphylococcus aureus* (MRSA). A rapid chromogenic response was achieved by localizing the dye at the surface of core-shell fibers, resulting in a 5× faster response relative to conventional nanofibers. By incorporating polyvinylpyrrolidone (PVP) dopant in the shell, the sensitivity was boosted to enable detection of bacteria at clinically relevant concentrations after 2 h exposure: $2.5\times10^5$ CFU/cm$^2$ *P. aeruginosa* and $1.0\times10^6$ CFU/cm$^2$ MRSA. Introduction of PVP in the shell also boosted the degree of hydrolysis of the chromogenic probe by a factor of 1.2× after 3 h exposure to a low concentration of *P. aeruginosa* ($10^5$ CFU/cm$^2$). PVP was also found to improve the discernibility of the color change at high bacterial concentrations. FIG. 5 illustrates the electrospinning method used to produce core-shell nanofibers mats by researchers at University of Manitoba for wound dressing applications as reported by Abdali, et. el. and also Currie, et al.

An electrospinning apparatus developed by the National Aeronautics and Space Administration (NASA) is directed to producing larger size fiber mats comprising aligned fibers. NASA's Langley Research Center created a modified electrospinning apparatus (shown in FIG. 6) for spinning highly aligned polymer fibers as disclosed in U.S. Pat. No. 7,993,567. NASA developed an apparatus that uses an auxiliary counter electrode to align fibers for control of the fiber distribution during the electrospinning process. The electrostatic force imposed by the auxiliary electrode creates a converged electric field, which affords control over the distribution of the fibers on the rotating collector surface. A polymer solution is expelled through the tip of the spinneret (i.e. emitter) at a set flow rate as a positive charge is applied. An auxiliary electrode, which is negatively charged, is positioned opposite the charged spinneret. The disparity in charges creates an electric field that effectively controls the behavior of the polymer jet as the jet is expelled from the spinneret. The electric field controls the distribution of the fibers and mats formed from the polymer solution as fibers land on a rotating collection mandrel (i.e. drum collector). The disclosure recites "Pseudo-woven mats were generated by electrospinning multiple layers in a 0°/90° lay-up. This was achieved by electrospinning the first layer onto a Kapton® film attached to the collector, manually removing the polymer film from the collector, rotating it 90°, reattaching it to the collector and electrospinning the second layer on top of the first, resulting in the second layer lying 90° relative to the first layer. Fibers were collected for one minute in each direction. A high degree of alignment was observed in this configuration. In order to assess the quality of a thicker pseudo-woven mat, the lay-up procedure was repeated 15 times in each direction (0°/90°) for a period of 30-60 seconds for each orientation, generating a total of 30 layers." The required and repeated step of "removing the polymer film, rotating it 90°, reattaching it to the collector and electrospinning the second layer on top of the first" is a major deficiency in the method and apparatus taught in the NASA'567 patent when considered from the perspective of cost-effective commercial production of cross-aligned nanofiber membranes. While the drum supports attached fibers and prevents layer destruction during rotation unlike the method reported by Zhang, et al., repeated manual removal of the Kapton® film reportedly results in some misalignment of the collected fibers, which distorts the cross-alignment of fibers in the resulting fiber mat. Further, the labor cost and production time associated with repeated manual removal of the Kapton® film and reattachment on the collector is cost prohibitive in commercial applications of electrospinning.

A method and apparatus to fabricate larger-size, well-structured membranes comprising cross-aligned electrospun fiber from many fiber branches, without fiber layer destruction and manual processes, has not been solved. Larger dimension membranes are needed for example in fabricating a range of fibrous drug delivery devices including devices used in wound care applications, as well as at least tissue engineering scaffolds, medical grade filters, and protective fabrics. A scalable method is needed by which uniformly distributed fiber can be deposited on a collector during electrospinning processes, achieving cross-aligned fiber deposition and larger-size fiber membranes absent manual intervention.

SUMMARY OF THE INVENTION

In one aspect, the present invention provides an apparatus for collecting fiber threads in an electrospinning device, the apparatus comprising an elongated assembly having a plurality of segments consisting of at least a first segment, a second segment, and an intermediate segment, the first segment positioned and connected at one end of the intermediate segment and the second segment positioned and connected at an opposite end of the intermediate segment, the first segment and second segment presenting a circumferential conductor at an edge.

In one aspect, each circumferential conductor is electrically chargeable and presents on the first and second segments one of an edge, a ribbon, or a disk.

In one aspect, the present invention collects fiber from at least one emitter electrospinning nanoscale fiber streams comprising many charged fiber branches, where the at least one emitter is electrically chargeable and has a tip positioned offset, away from, and between a circumferential conductor on the first segment and the circumferential conductor on the second segment.

In another aspect, the present invention provides a segmented collector as an elongated assembly mountable on a support structure for rotating the elongated assembly about a longitudinal axis, where the circumferential conductor on the first segment and the circumferential conductor on the second segment is either electrically grounded or an electrical charged, the electrical charge on the edge conductor when charged being an opposite polarity relative to a charge applied to the at least one fiber emitter and the elongated assembly holds collected fibers when grounded during rotation.

In one aspect, the present invention provides a method and apparatus for bi-directional attraction of electrospun fibers discharged from at least one emitter, attracting fibers toward at least one circumferential conductor on each of at least the first segment and the second segment, and attracting fibers discharged toward at least one electrically chargeable steering electrode, the circumferential conductors and the at least one steering electrode being chargeable with an electrical polarity opposing a charge applied to the at least one fiber emitter.

In one aspect, the present invention provides a method and apparatus to fabricate well-structured membranes comprising cross-aligned nanofibers that provide optimal porosity for cell migration and exudate flow from a wound, maximize surface contact with a wound, and support triggered release of biocides in the presence of infection, where the angular cross-alignment relationship between aligned nanofibers in adjacent layers is alterable by increasing or decreasing the rotation speed of the elongated assembly about a longitudinal axis.

In another aspect, the present invention provides a method and apparatus for cost-effective fabrication of cross-aligned nanofiber membranes of varying dimensions usable as an inner layer in wound care dressings, including for example wound care dressings for treatment of both full and partial thickness burns and ulcerated skin, as well as acute and trauma injury.

In one aspect, the present invention provides a method and apparatus for fabricating larger-size, fibrous membranes comprising cross-aligned nanofibers, and where manual steps in fiber deposition on a the collector are eliminated to provide an efficient, commercially viable process for use in producing at least a fibrous drug delivery membrane, wound care dressing, or a tissue engineering scaffold.

In another aspect, the present invention provides a method and apparatus for fabricating nanofiber membranes of varying dimensions, the apparatus comprising segments that are interchangeably re-configurable to enable fabrication of membranes of different sizes, where membrane dimensions are alterable by increasing or decreasing at least one of the diameter of the segmented collector or the separation distance between the first and second segments of the segmented collector.

In one aspect, the apparatus of the present invention comprises an elongated assembly having a plurality of segments consisting of at least a first segment, a second segment, a third segment, a fourth segment, and an intermediate segment, where the first segment and third segment are positioned at one end of the intermediate segment and the second segment and fourth segment are positioned at an opposite end of the intermediate segment, the segment positioning being interchangeable, and each segment except the intermediate segment presents an electrically chargeable circumferential conductor to electrospun nanofibers, and the elongated assembly when charged or grounded holds collected fibers in position during rotation.

In one aspect, the first segment and the second segment may comprise at least thin metallic disks each rotationally mountable on a separate drive motor or on a common shaft, and moveably separable on a base mount or shaft to accept the intermediate segment between the first segment and the second segment (i.e., disks).

In one aspect, the intermediate segment may comprise a metallic cylinder or drum that connects to the first and second segments (i.e., disks) using insulating connectors. The length of the intermediate segment (i.e., cylinder) mounted between the first and second segments (i.e., disks) determines the width of the membrane that can be fabricated.

In one aspect, the width dimension of the membrane may be altered by inserting intermediate segments of alternate lengths, and the diameters of the intermediate segment and first and second segments can be adjusted to determine the length of the membrane that can be fabricated.

In one aspect, the present invention provides a segmented collector useable in an electrospinning device configured with one or a plurality of steering electrodes, the steering electrodes being programably chargeable so that elliptical motion pathways of emitter fiber streams toward the electrodes from the at least one electrically chargeable emitter are alterable.

In another aspect, the present invention provides a segmented collector useable in an electrospinning device presenting a plurality of programably chargeable conductors on collector segments adding to the number of segments positioned toward each end of the elongated assembly (i.e., collector), each conductor on each segment being electrically chargeable and separated from an adjacent segment by a finite distance.

In another aspect, the present invention provides an apparatus and method for controlling collection of fibers on a segmented collector by at least one of altering the electrical charge on the edge conductors, removing the electrical charge from the edge conductors, and electrically grounding said edge conductors, where the edge conductors are electrically isolated from the intermediate segment of the segmented collector.

In one aspect, the plurality of programably chargeable conductors may comprise metallic ribbons or edges circumferentially engaging and electrically insulated from the surface of the elongated assembly (i.e., collector).

In one aspect, the plurality of programably chargeable conductors may comprise connectable disks for positioning at one end of at least the first segment and the second segment, and being electrically insulated therefrom.

In another aspect, the fiber collector provided by the present invention may be used in an electrospinning device where a controller is included for governing the charge status of chargeable components of the device, the chargeable components receiving an electrical charge from a high-voltage power supply, and the charge status of conductors (i.e., edge conductors, ribbons, disks) on the first segment and the second segment and extensions, as well as the charge status of one or a plurality of steering electrodes, being determined by the controller.

In another aspect, the fiber collector provided by the present invention may be used in an electrospinning device where at least one steering electrode or a plurality of steering electrodes is fixedly mounted in-line with the emitter.

In another aspect, the fiber collector provided by the present invention may be used in an electrospinning device where at least one steering electrode is movably mounted on a robotic arm for repositioning with respect to the emitter and the elongated assembly. A plurality of electrodes may also be mounted on the robotic arm.

In another aspect, the fiber collector provided by the present invention may be used in an electrospinning device where at least one emitter (i.e., spinneret) or a plurality of emitters is fixedly mounted in-line with the at least one steering electrode.

In another aspect, the fiber collector provided by the present invention may be used in an electrospinning device adapted with at least one emitter (i.e., spinneret) configured to produce electrospun core-shell nanofibers, the core and the shell comprising differing material compositions or differing chemical compositions as necessary to produce fibrous membranes exhibiting novel characteristics.

In another aspect, the present invention provides an apparatus and method to form multiple fiber layers as a membrane, said fibers in each layer being cross-aligned at one of orthogonal or oblique angles relative to fibers in adjacent layers, where the cross-alignment angle is alterable by at least one of repositioning a steering electrode or altering the rotation speed of the segmented collector of the present invention while electrospinning nanofibers onto the segmented collector.

DETAILED DESCRIPTION OF PREFERRED EMBODIMENTS OF THE INVENTION

Figure 1:
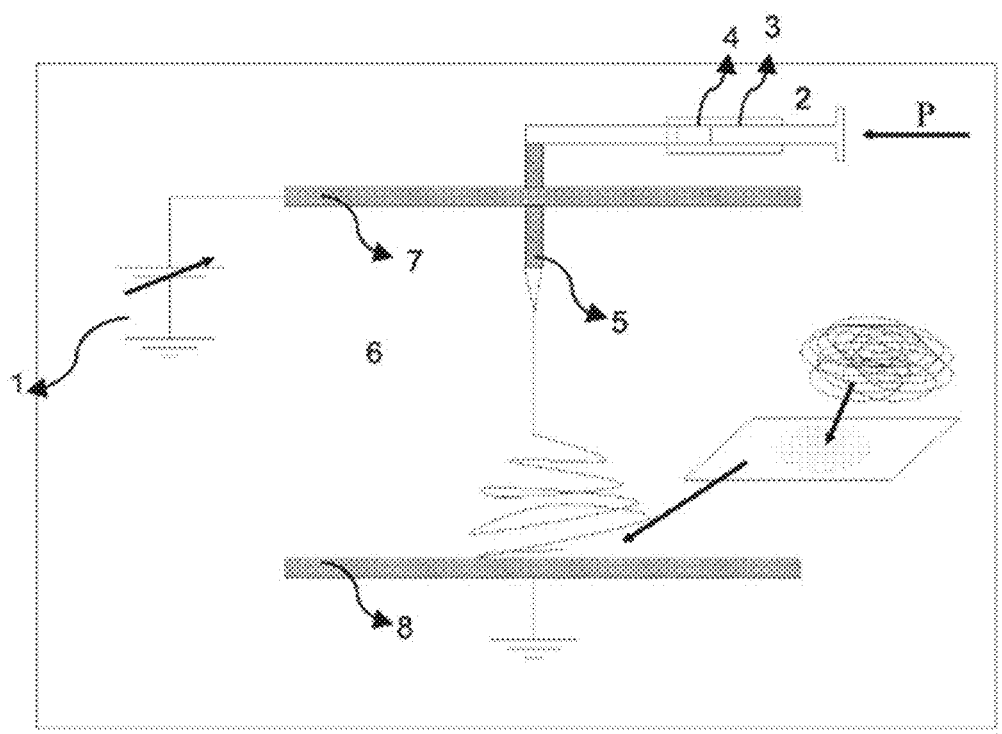
FIG. 1 is a diagram schematically illustrating the method of an electrospin process using a target plate as exemplified in U.S. Patent Application 20100112020.

In brief:

FIG. 1 is a diagram schematically illustrating the method of a typical electrospin process using a target plate as exemplified in U.S. Patent Application 20100112020. A typical electrospin setup of this type consists essentially of syringe pump, syringe with a needle, high-voltage power supply, and a flat plate collector. The syringe needle is electrically charged by applying a high-voltage in the range of 5 KVA to 20 KVA produced by a power supply. The collector plate is typically grounded. Collected fibers are randomly oriented on the collector plate.

Figure 2:
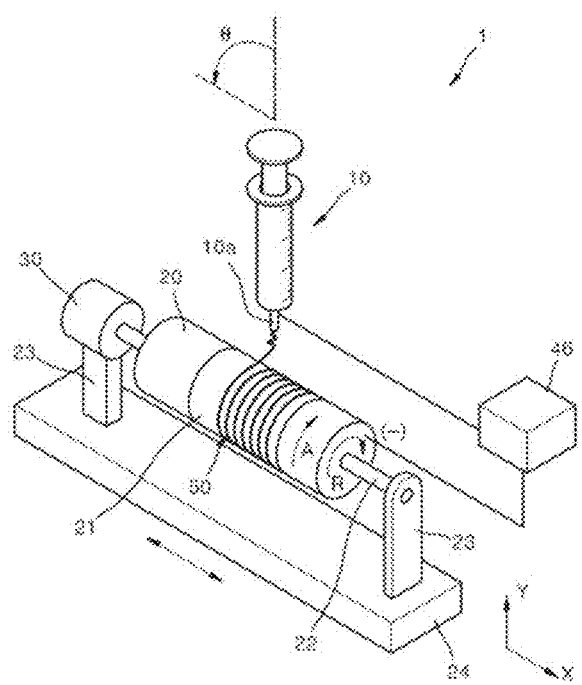
FIG. 2 is a diagram schematically illustrating the method of an electrospin process using a drum collector as taught in Korean Patent KR101689740.

FIG. 2 is a diagram schematically illustrating the method of an electrospin process using a drum collector as taught in Korean Patent KR101689740. A typical electrospin setup of this type consists essentially of syringe pump, syringe with a needle, high-voltage power supply, and rotating drum collector. The syringe needle is electrically charged by applying a high-voltage typically in the range of 5 KVA to 20 KVA produced by a power supply. The drum collector is typically grounded. Collected fiber wrap around the drum and may be generally aligned in one direction as shown or rather randomly oriented.

Figure 3A:
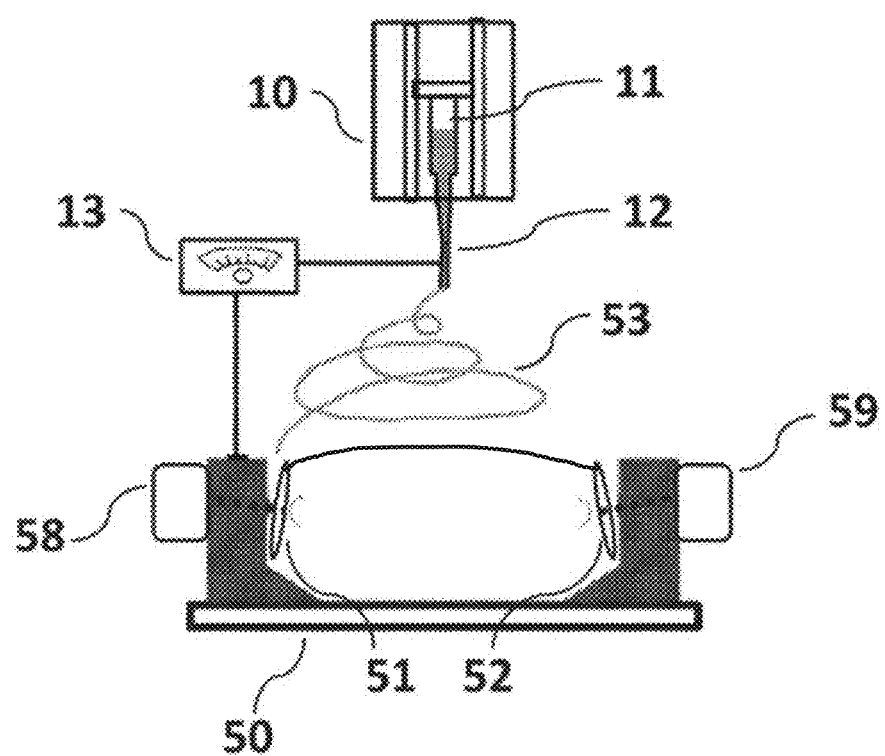
FIG. 3A is a diagram schematically illustrating the method of an electrospin process using a pair of charged opposing disks in fiber collection as taught in U.S. Pat. No. 9,359,694.

FIG. 3A is a diagram schematically illustrating the method of an electrospin process using a pair of charged opposing disks in fiber collection as taught in U.S. Pat. No. 9,359,694. The electrospin setup of this type consists essentially of syringe pump, syringe with a needle, high-voltage power supply, and a pair of collector disks. The syringe needle is electrically charged by applying a high-voltage typically in the range of 5 KVA to 20 KVA produced by a power supply. The collector disks are may be charged or grounded. The collected fibers are generally aligned in one direction and harvested with a robotic arm holding a substrate (not shown).

Figure 3B:
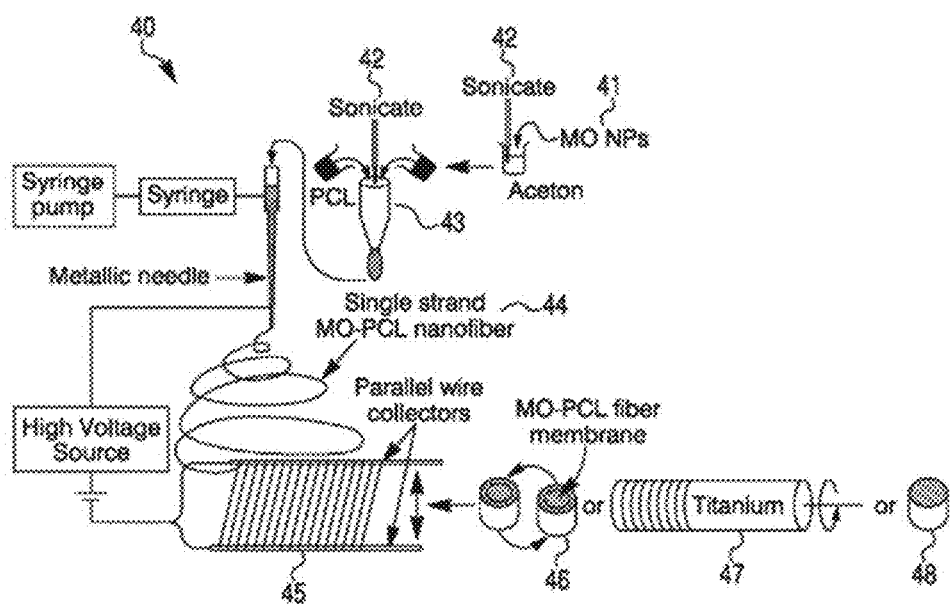
FIG. 3B is a diagram schematically illustrating the method of an electrospin process using a pair of charged collector wires as taught in U.S. Pat. No. 9,809,906.

FIG. 3B is a diagram schematically illustrating the method of an electrospin process using a pair of charged collector wires as taught in U.S. Pat. No. 9,809,906. A typical electrospin setup of this type consists essentially of syringe pump, syringe with a needle, high-voltage power supply, and a pair of collector wires. The syringe needle is electrically charged by applying a high-voltage typically in the range of 5 KVA to 20 KVA produced by a power supply. The collector wires may also be grounded. The collected fibers are generally aligned in one direction and manually harvested.

Figure 4:
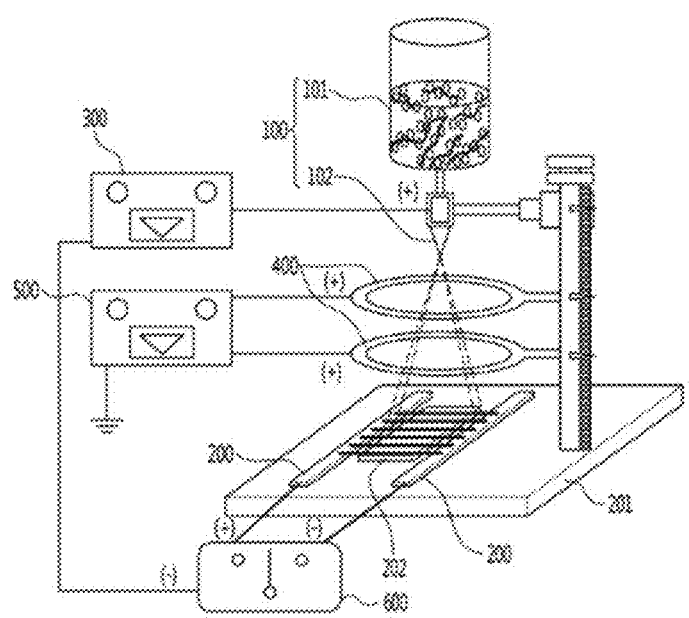
FIG. 4 is a diagram illustrating the method of an electrospin process using two parallel plates as taught in Korean Patent KR101224544.

FIG. 4 is a diagram schematically illustrating the method of an electrospin process using two parallel plates as taught in Korean Patent KR101224544. A typical electrospin setup of this type consists essentially of syringe pump, syringe with a needle, high-voltage power supply, and a pair of charged or electrically grounded collectors which may be parallel plates as shown. The syringe needle is electrically charged by applying a high-voltage typically in the range of 5 KVA to 20 KVA produced by a power supply. The collector plates are typically grounded. The collected fibers are generally aligned in one direction and may be harvested by placing a substrate between the plates and below the collected fibers as shown. Achieving fiber cross alignment of fibers on the substrate requires rotation of the substrate.

Figure 5:
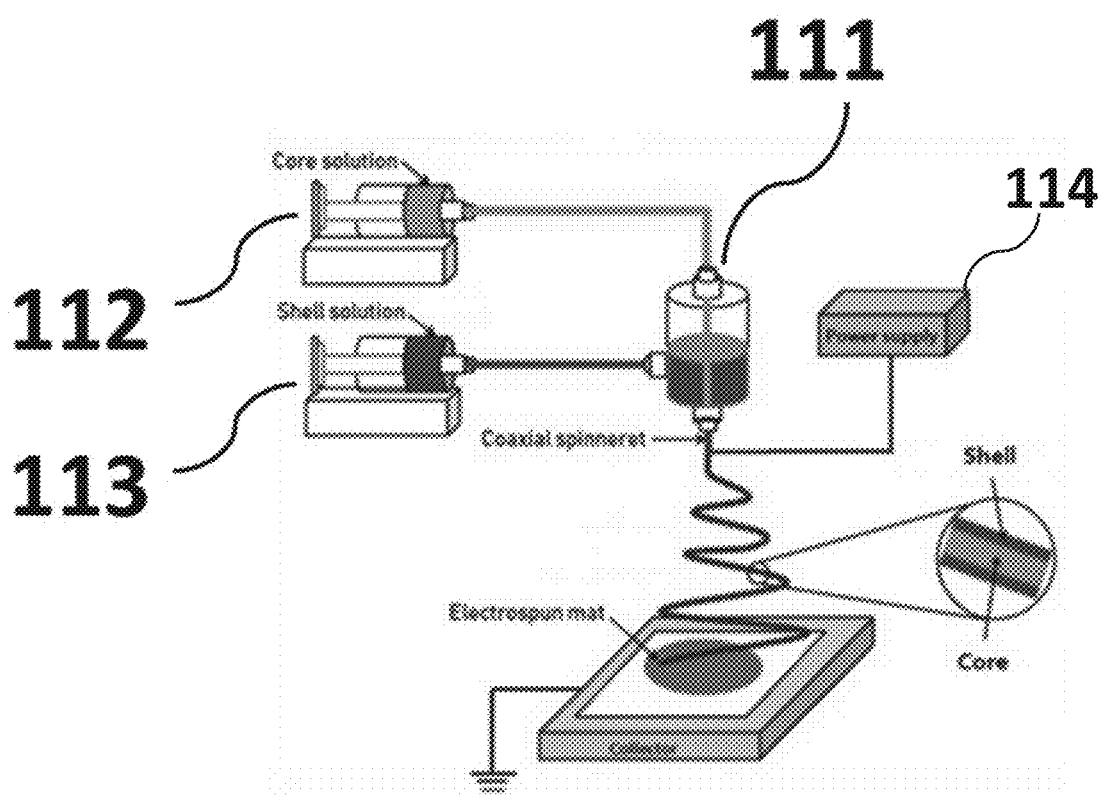
FIG. 5 is a diagram illustrating a typical electrospinning setup for producing coaxial fibers collected on a flat plate.

FIG. 5 is a diagram showing a typical coaxial electrospinning setup. A core-shell configuration uses a coaxial nozzle comprising a central tube surrounded by a concentric circular tube. Two different polymer solutions are pumped into the coaxial nozzle separately, and ejected from the charged emitter simultaneously. A Taylor cone is formed when a high voltage is applied between the spinneret and the collector. Inner and outer solutions in the form of a jet are ejected towards a charged collector. The solvent in the solution jet evaporates, forming the core-shell nanofibers. Each embodiment of the present invention can be used as a fiber collector in an electrospining device configured to produce solid or core-shell nanofibers using electrospinning components similar to those shown.

Figure 6:
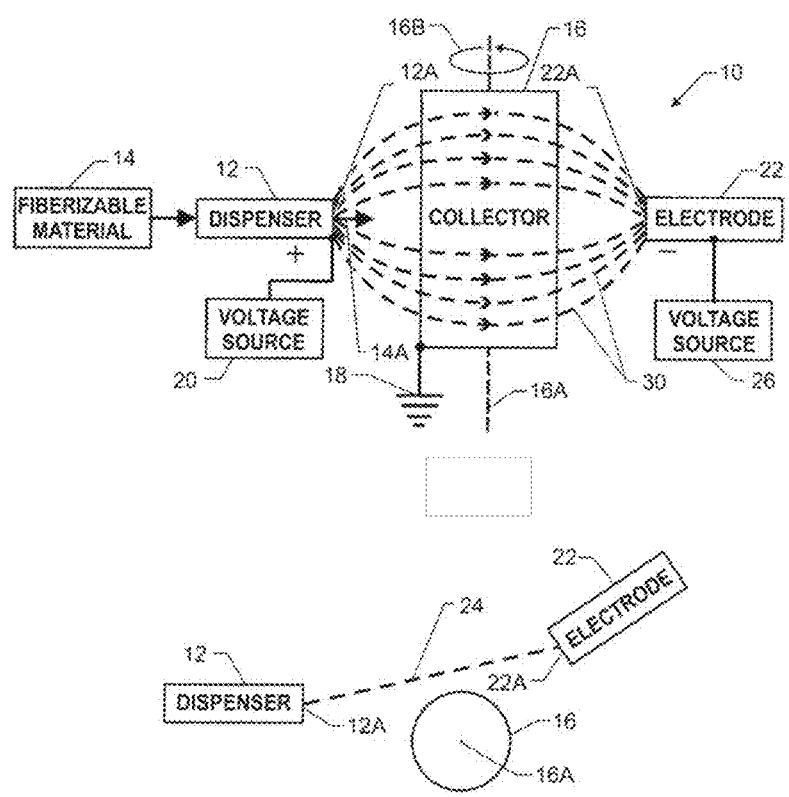
FIG. 6 is diagram showing the electrospinning apparatus developed by NASA and disclosed in U.S. Pat. No. 7,993,567.

FIG. 6 is a diagram showing an electrospinning apparatus developed by NASA and disclosed in U.S. Pat. No. 7,993,567. The apparatus uses an auxiliary counter electrode to align fibers for control of the fiber distribution during the electrospinning process. The electrostatic force imposed by the auxiliary electrode creates a converged electric field, which affords control over the distribution of the fibers on the rotating collector surface. A polymer solution is expelled through the tip of the spinneret at a set flow rate as a positive charge is applied. An auxiliary electrode, which is negatively charged, is positioned opposite the charged spinneret. The disparity in charges creates an electric field that effectively controls the behavior of the polymer jet as it is expelled from the spinneret; it ultimately controls the distribution of the fibers and mats formed from the polymer solution as it lands on a rotating collection mandrel. Cross-alignment of fibers requires use of a collection film mounted on the mandrel, and manual removal and rotation of the film between deposition of each fiber layer.

Figure 7:
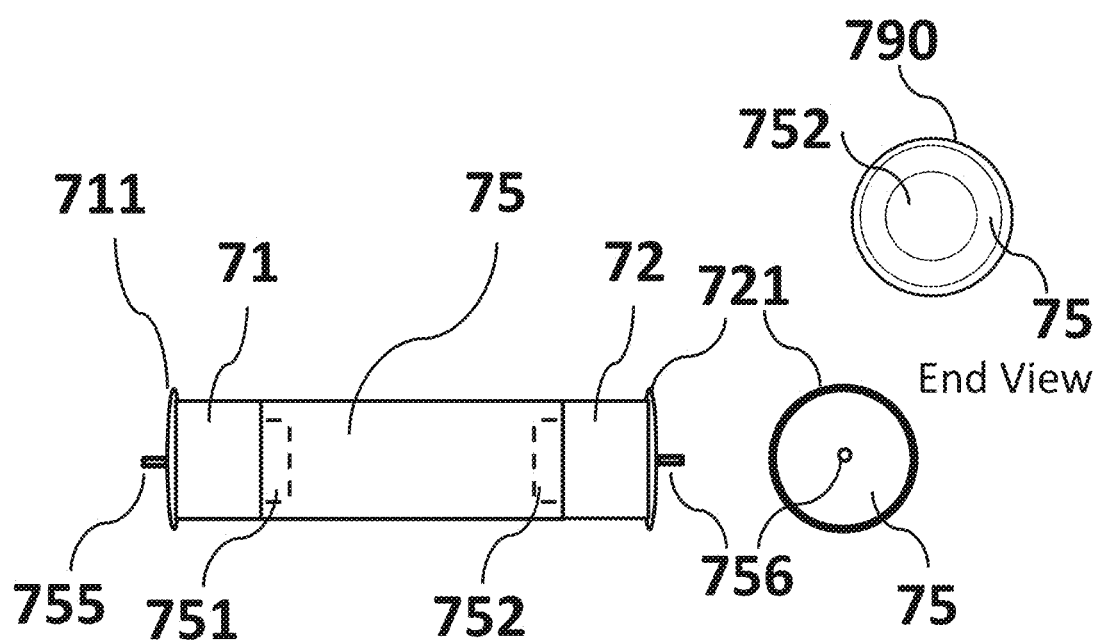
FIG. 7 is a non-limiting diagram showing components of an embodiment of the present invention comprising a first segment, a second segment and an intermediate segment.

FIG. 7 is a non-limiting diagram showing components of an embodiment of the present invention comprising a first segment, a second segment and an intermediate segment, the first segment and the second segment each configured with electrically chargeable conductors. The embodiment shown in the diagram includes an electrically chargeable edge conductor circumferentially resident on the first segment, and an electrically chargeable edge conductor circumferentially resident on the second segment. The edge conductors are electrically insulated from the first and second segments. The intermediate segment is positioned and connected between the first segment and the second segment to collectively present an elongated cylindrical structure. The first segment, the second segment, and the intermediate segment may be electrically grounded or floating.

Figure 8:
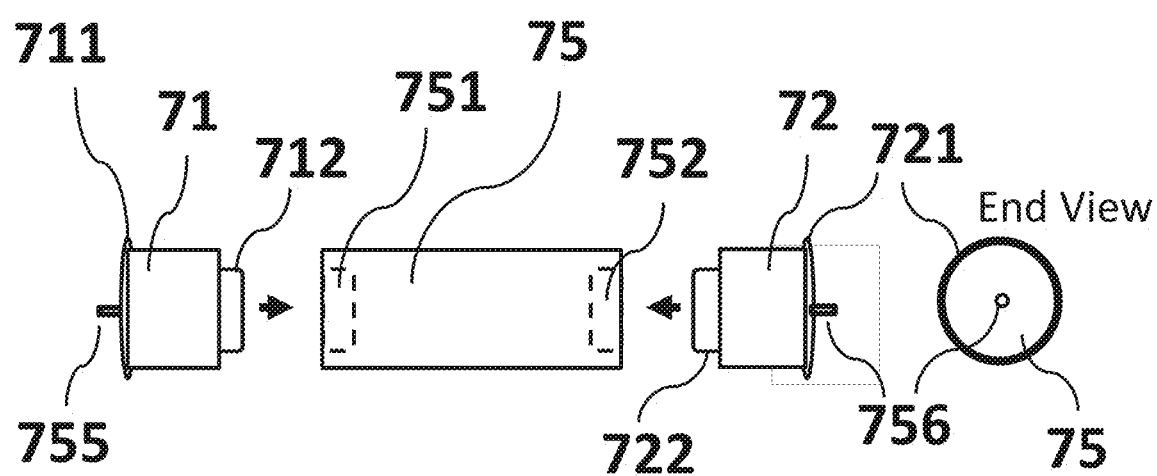
FIG. 8 is a non-limiting diagram showing components of an embodiment of the present invention comprising a first segment, a second segment and an intermediate segment, where the first segment and the second segment are detached (i.e., separated) from the intermediate segment.

FIG. 8 is a non-limiting diagram showing components of an embodiment of the present invention comprising a first segment, a second segment and an intermediate segment, where the first segment and the second segment are disconnected and separated from the intermediate segment. The embodiment shown in the diagram includes an electrically chargeable edge conductor circumferentially resident on the first segment, and an electrically chargeable edge conductor circumferentially resident on the second segment. The edge conductors are electrically insulated from the first and second segments. As shown, the first segment and the second segment may be removably connected to the intermediate segment to collectively present an elongated cylindrical structure. The elongated cylindrical structure may be configured in a range of different diameters (e.g., 1 cm to 20 cm) and lengths (e.g., 3 cm to 20 cm) to enable fabrication of cross-aligned nanofiber membranes of different dimensions. The first segment, the second segment, and the intermediate segment may be electrically grounded or floating.

Figure 9:
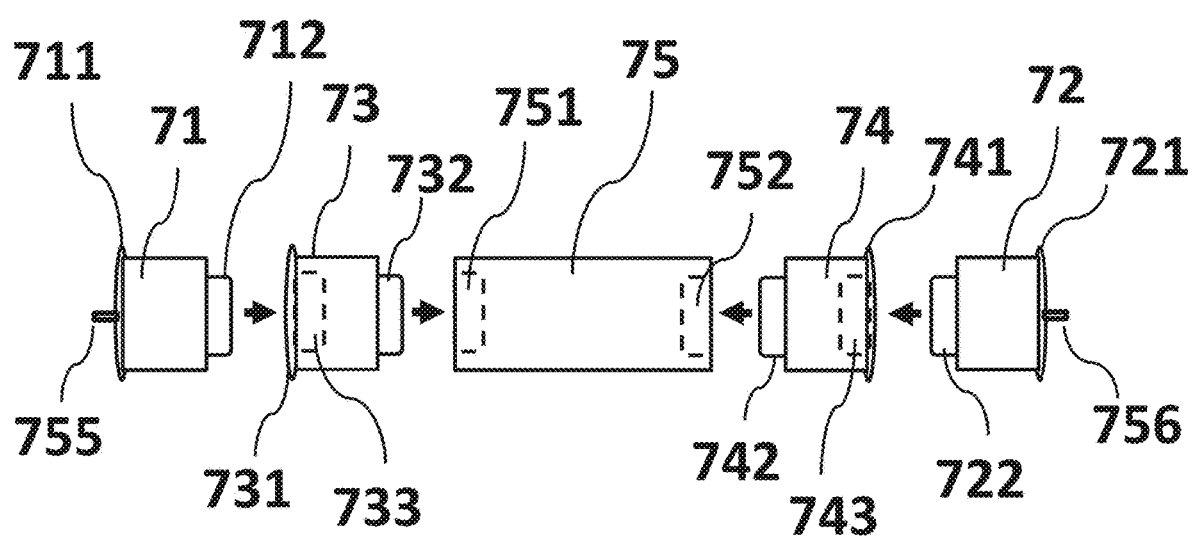
FIG. 9 is a non-limiting diagram showing components of an embodiment of the present invention comprising a first segment, a second segment, a third segment, a fourth segment, and an intermediate segment, where the first segment, the second segment, the third segment, the fourth segment, and the intermediate segment are detached (i.e., separated).

FIG. 9 is a non-limiting diagram showing components of an embodiment of the present invention comprising a first segment, a second segment, a third segment, a fourth segment, and an intermediate segment, where the first segment, the second segment, the third segment, the fourth segment, and the intermediate segment are disconnected and separated. The embodiment shown in the diagram includes an electrically chargeable edge conductor circumferentially resident on the first segment, the second segment, the third segment, and the fourth segment. The edge conductors are electrically insulated from the first segment, the second segment, the third segment, and the fourth segment. As shown, the first segment, the second segment, the third segment, the fourth segment, and the intermediate segment may be removably connected to each other to collectively present an elongated cylindrical structure. The first segment, the second segment, the third segment, the fourth segment, and the intermediate segment may be electrically grounded or floating.

Figure 10:
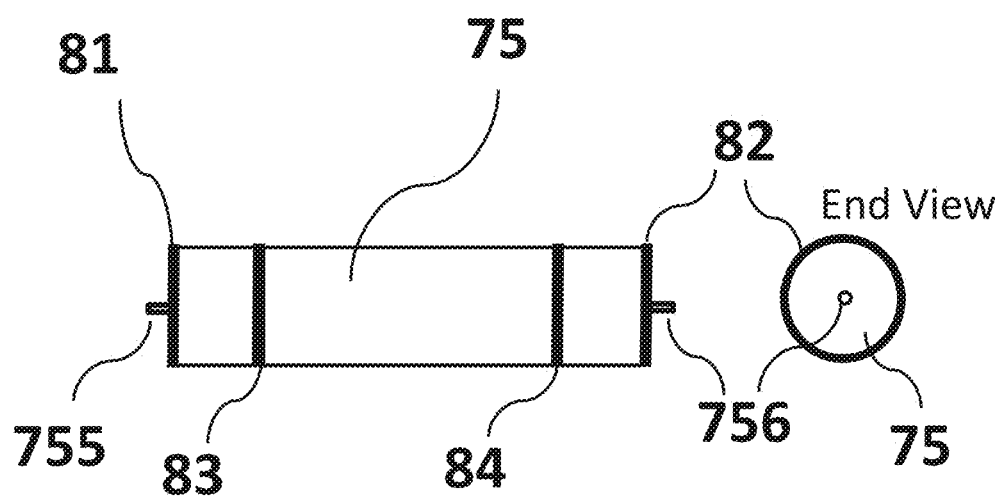
FIG. 10 is a non-limiting diagram showing components of an embodiment of the present invention comprising a first segment (i.e., metallic ribbon), a second segment (i.e., metallic ribbon), a third segment (i.e., metallic ribbon), and a fourth segment (i.e., metallic ribbon), where the metallic ribbons are circumferentially mounted on the intermediate segment.

FIG. 10 is a non-limiting diagram showing components of an embodiment of the present invention configured with a first segment as a metallic ribbon, a second segment as a metallic ribbon, a third segment as a metallic ribbon, and a fourth segment as a metallic ribbon, where the metallic ribbons are circumferentially mounted on and electrically insulated from the intermediate segment. A plurality of nanofibers may be attracted to and attach to either the first segment (i.e., metallic ribbon) and the second segment (i.e., metallic ribbon), or attracted to and attach between the third segment (i.e., metallic ribbon) and the fourth segment (i.e., metallic ribbon), spanning across the length of the intermediate segment (i.e., an elongated cylinder) between charged ribbon pairs.

Figure 11:
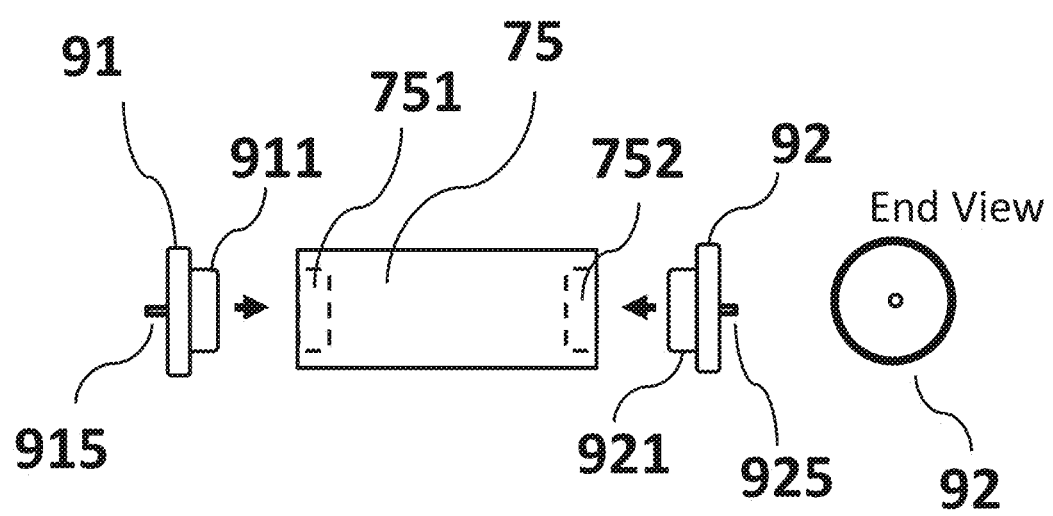
FIG. 11 is a non-limiting diagram showing components of an embodiment of the present invention configured with a first segment (i.e., metallic disk), a second segment (i.e., metallic disk) attached to an intermediate segment (e.g., an elongated cylinder).

FIG. 11 is a non-limiting diagram showing components of an embodiment of the present invention configured with a first segment as a metallic disk, a second segment as a metallic disk, both segments removably connectable to an intermediate segment (i.e., an elongated cylinder). A plurality of nanofibers may be attracted to and attach to the first segment (i.e., metallic disk) and the second segment (i.e., metallic disk), spanning across the length of the intermediate segment (i.e., an elongated cylinder).

Figure 12:
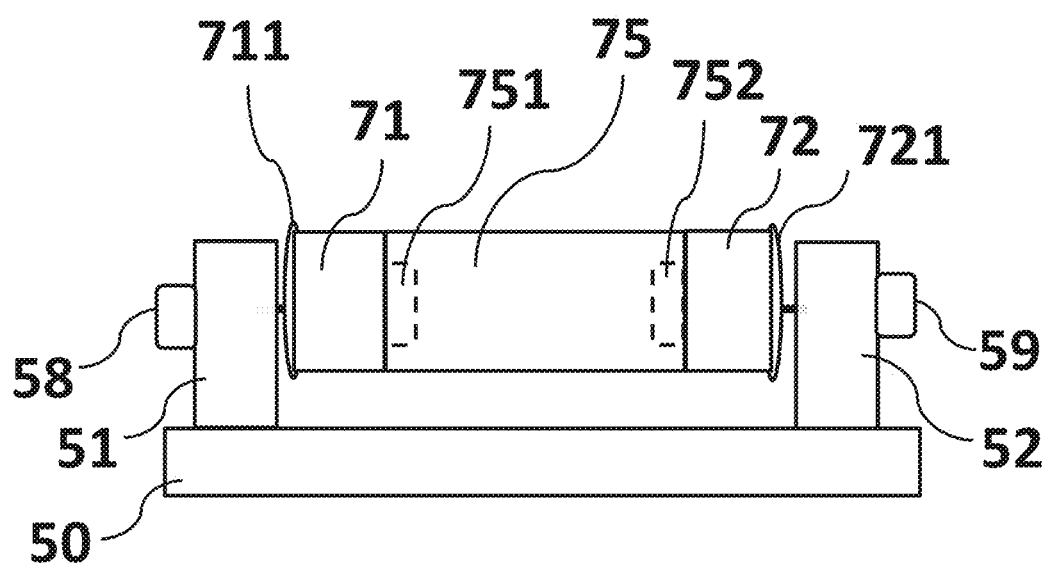
FIG. 12 is a non-limiting diagram showing components of an embodiment of the present invention comprising an intermediate segment positioned between a first segment and a second segment to collectively present an elongated cylindrical structure mounted as a fiber collector on a drive unit.

FIG. 12 is a non-limiting diagram showing components of an embodiment of the present invention comprising an intermediate segment positioned between a first segment and a second segment to collectively present an elongated cylindrical structure mounted as a fiber collector on a drive unit. The cylindrical structure may be rotated by the drive unit around a longitudinal axis aligned through the center and extending through the length of the cylindrical structure. The embodiment shown in the diagram includes an electrically chargeable edge conductor circumferentially resident on the first segment, and an electrically chargeable edge conductor circumferentially resident on the second segment.

Figure 13:
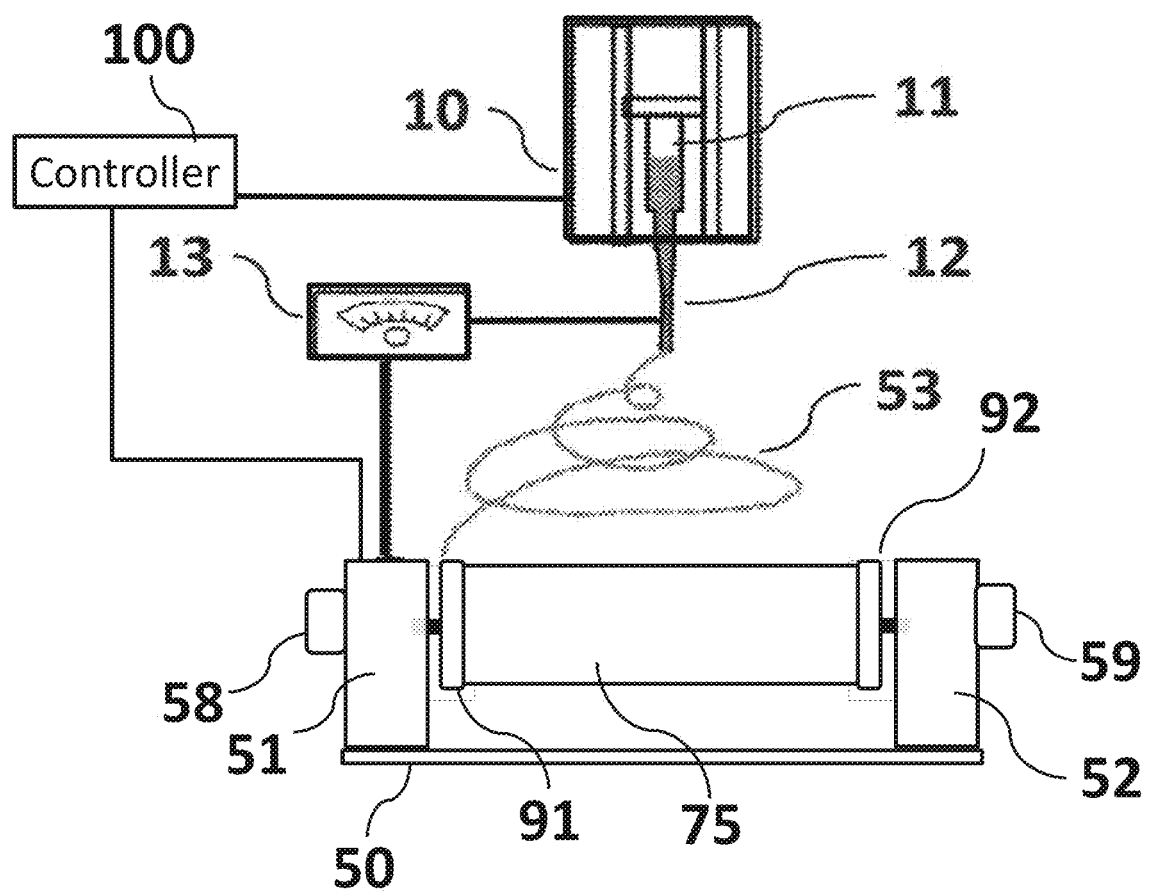
FIG. 13 is a non-limiting diagram showing an embodiment of the present invention installed in an electrospinning device as a fiber collector configured with a first segment (i.e., a disk), a second segment (i.e., a disk), and an intermediate segment (i.e., an elongated cylinder).

FIG. 13 is a non-limiting diagram showing an embodiment of the present invention installed in an electrospinning device. An embodiment of the present invention is shown comprising a first segment (i.e., a disk), a second segment (i.e., a disk), and an intermediate segment (i.e., an elongated cylinder). The intermediate segment connects to the first segment and the second segment using insulating connectors (FIG. 11). The first segment and the second segment are electrically chargeable. The intermediate segment can be charged, maintained electrically neutral, or at electrically grounded. The first segment and the second segment may be mounted on separately controlled drive motors that are movably mounted on a base. The span between the first segment and the second segment may be increased to enable mounting the intermediate segment on the insulating connectors.

Figure 14:
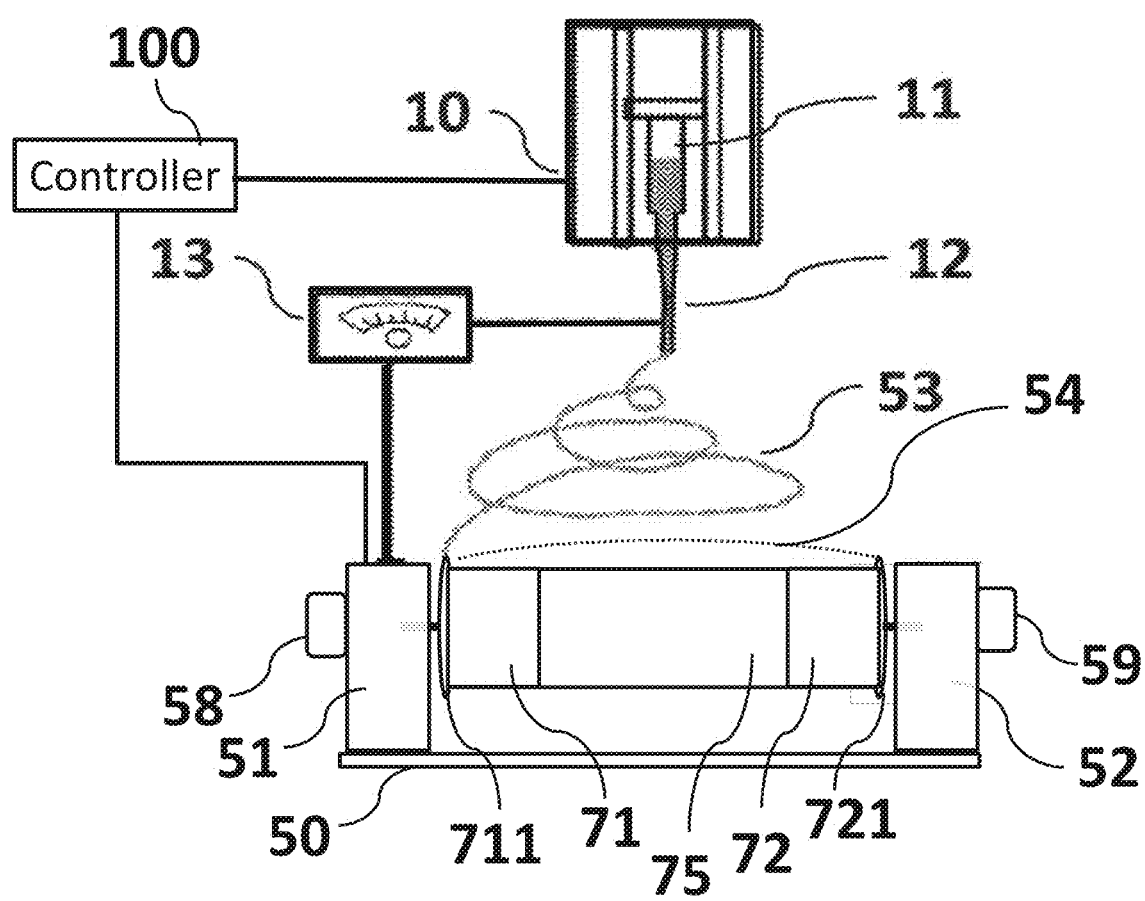
FIG. 14 is a non-limiting diagram showing an embodiment of the present invention installed in an electrospinning device as a fiber collector, where a nanofiber is attached between a first segment edge conductor and the second segment edge conductor, spanning across the length of the intermediate segment (i.e., an elongated cylinder).

FIG. 14 is a non-limiting diagram showing an embodiment of the present invention where a nanofiber is attached between a first segment configured with an edge conductor and a second segment configured with an edge conductor, spanning across the length of the intermediate segment (i.e., an elongated cylinder). The charged electrospun fiber is attracted to the first segment edge conductor and the second segment edge conductor, which are charged at an opposite polarity with respect to the charged fiber. The whipping action characteristic of electrospun fibers causes the fiber to move back and forth, the fiber attaching to points circumferentially presented on the first segment edge conductor and the second segment edge conductor during rotation.

Figure 15:
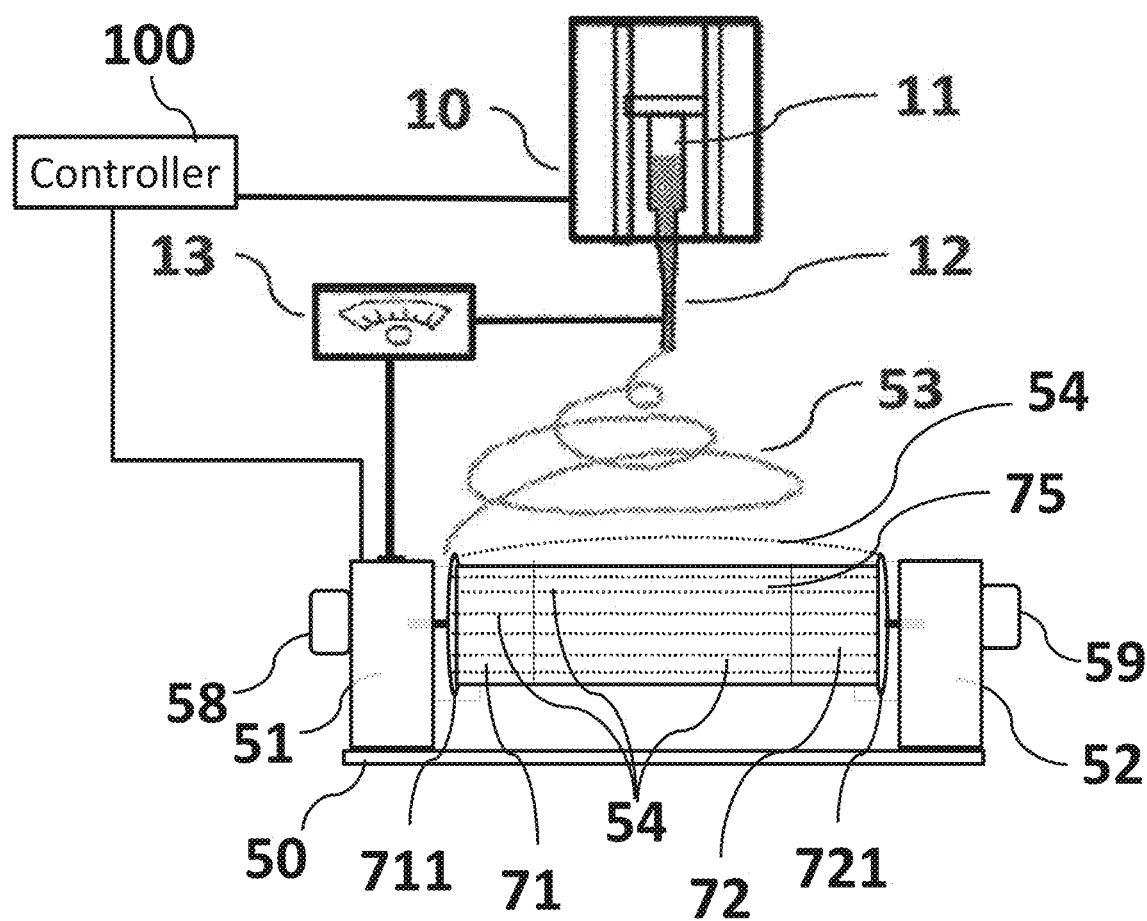
FIG. 15 is a non-limiting diagram showing an embodiment of the present invention installed in an electrospinning device as a fiber collector, where a plurality of nanofibers is attached between a first segment edge conductor and a second segment edge conductor, spanning across the length of an intermediate segment (i.e., an elongated cylinder).

FIG. 15 is a non-limiting diagram showing an embodiment of the present invention where a plurality of nanofibers is attached between a first segment edge conductor and a second segment edge conductor, spanning across the length of the intermediate segment (i.e., an elongated cylinder). The charged electrospun fiber is attracted to the first segment edge conductor and the second segment edge conductor, which are charged at an opposite polarity with respect to the charged fiber. The whipping action characteristic of electrospun fibers causes the fiber to move back and forth the fiber attaching to points circumferentially presented on the first segment edge conductor and the second segment edge conductor during rotation. The first segment, the intermediate segment, and the second segment are collectively rotated by at least one drive motor about a longitudinal axis. Nanofibers attach at multiple points around the perimeter of the first segment edge conductor and the second segment edge conductor, spanning the separation space occupied by the intermediate segment.

Figure 16:
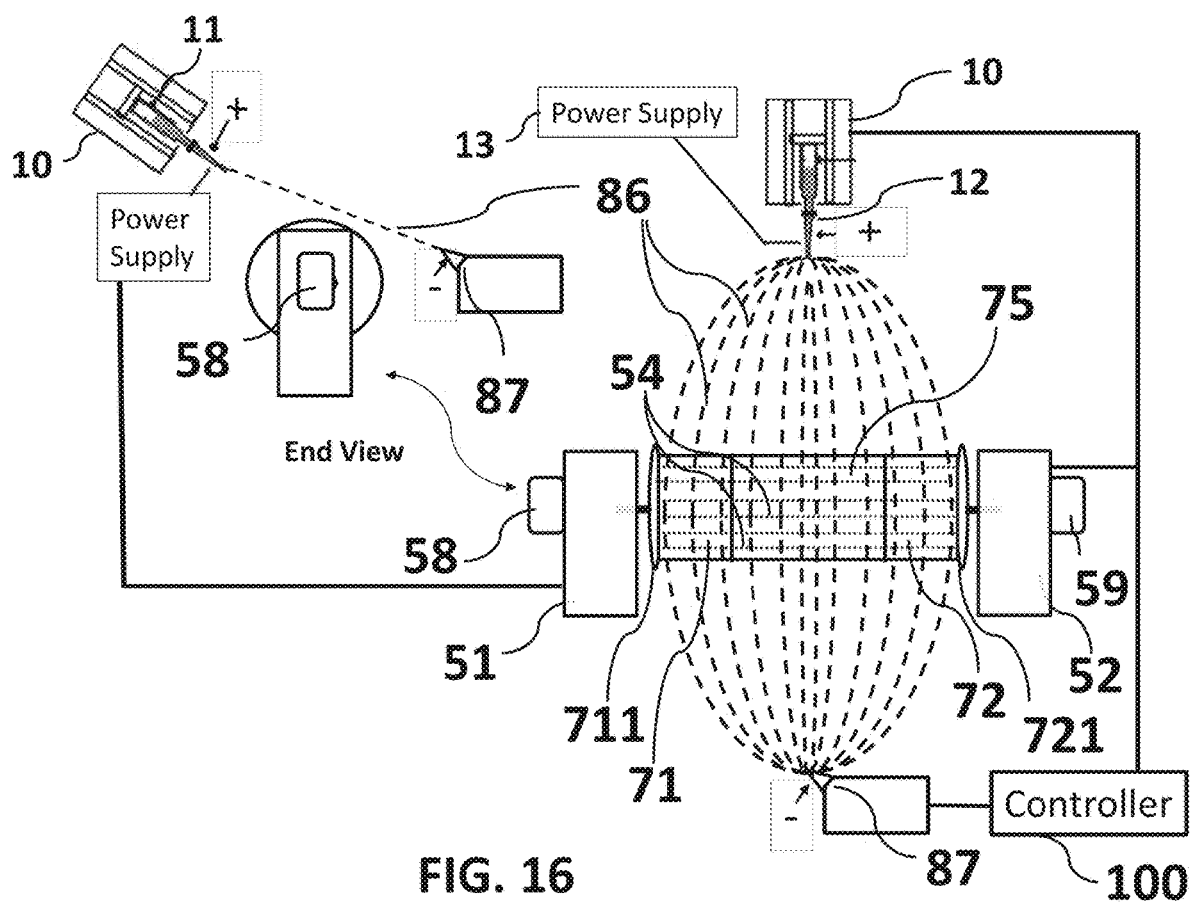
FIG. 16 is a non-limiting diagram showing an embodiment of the present invention installed in an electrospinning device as a fiber collector, where a plurality of nanofibers is attached between a first segment edge conductor and a second segment edge conductor), spanning across the length of an intermediate segment (i.e., an elongated cylinder), and a plurality of branched fibers are attracted between a charged emitter and a steering electrode having an opposing charge, the branched fibers spanning orthogonally across and proximate to the nanofibers attached to the first and second segments.

FIG. 16 is a non-limiting diagram showing an embodiment of the present invention where a plurality of nanofibers is attached between a first segment configured with an edge conductor and a second segment configured with an edge conductor, spanning across the length of an intermediate segment (i.e., an elongated cylinder), the nanofibers being supported and held in place on the surface of the intermediate segment when it is electrically grounded. A plurality of branched fibers is shown attracted between a charged emitter and a steering electrode having an opposing charge, the branched fibers spanning orthogonally across and proximate to the nanofibers attached to edge conductors resident on the first and second segments. The emitter is configured for electrospinning nanoscale fiber streams comprising many charged fiber branches. The emitter can be electrically charged, and has a tip positioned offset away from and between the edge conductor of the first segment and the edge conductor of the second segment. A support structure is provided for rotating the elongated assembly (first segment, second segment, and intermediate segment) about a longitudinal axis and no electrical charge is applied to the first segment and second segment while the steering electrode is electrically charged. The electrically chargeable steering electrode is provided for attracting the fiber streams along motion pathways substantially orthogonal to motion pathways of fiber streams attracted to the edge conductors resident on the first and second segments spanning the intermediate segment. The fibers are attracted to and held at the surface of the intermediate segment as it is rotated and electrically grounded. Fibers aligned along the longitudinal axis are held in place on the surface of the electrically grounded intermediate segment during rotation.

Figure 17:
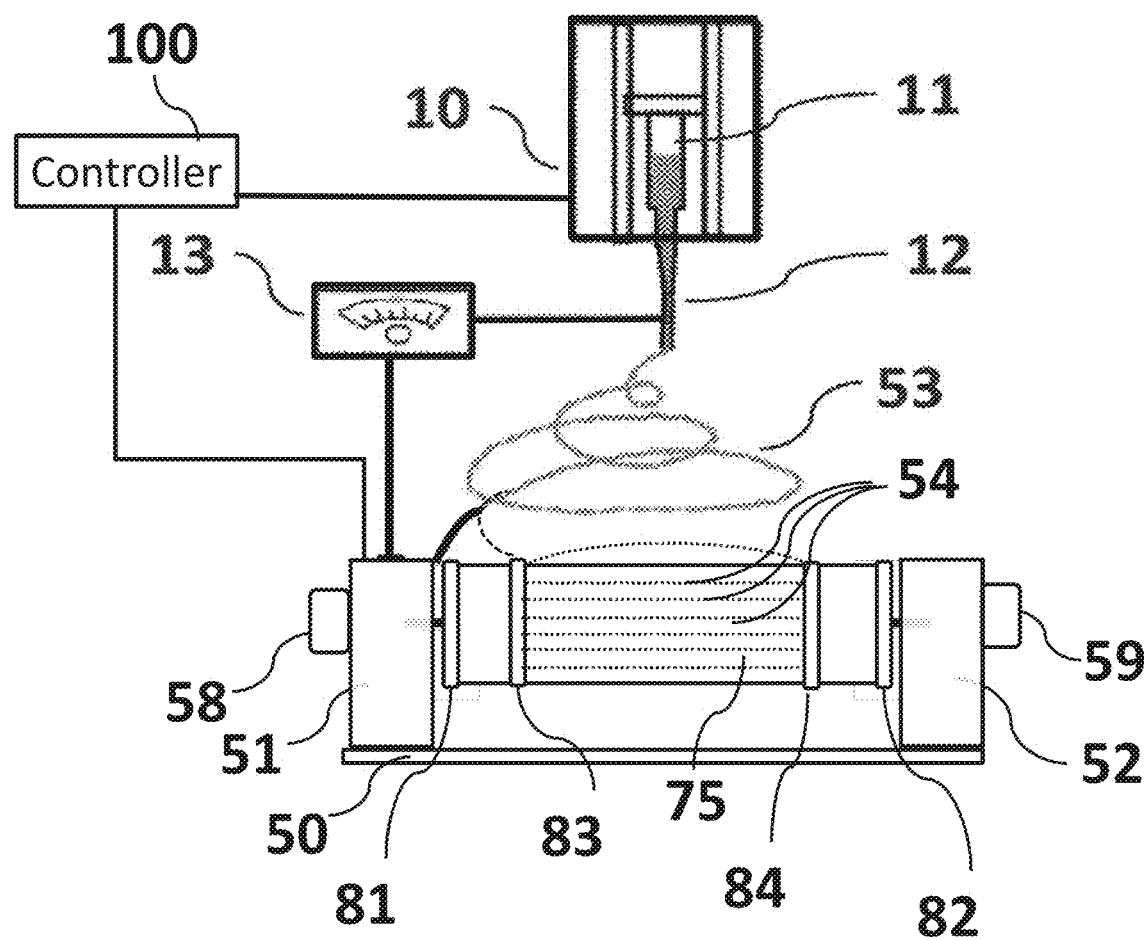
FIG. 17 is a non-limiting diagram showing an embodiment of the present invention installed in an electrospinning device as a fiber collector configured with a first segment (i.e., metallic ribbon), a second segment (i.e., metallic ribbon), a third segment (i.e., metallic ribbon), and a fourth segment (i.e., metallic ribbon), where a plurality of nanofibers is attached between the third segment (i.e., metallic ribbon) and the fourth segment (i.e., metallic ribbon), spanning across the length of the intermediate segment (i.e., an elongated cylinder).

FIG. 17 is a non-limiting diagram showing an embodiment of the present invention configured with a first segment (i.e., metallic ribbon), a second segment (i.e., metallic ribbon), a third segment (i.e., metallic ribbon), and a fourth segment (i.e., metallic ribbon), where a plurality of nanofibers is shown attached between the third segment (i.e., metallic ribbon) and the fourth segment (i.e., metallic ribbon), spanning across the length of the intermediate segment (i.e., an elongated cylinder). The charged electrospun fiber is attracted to the third segment (i.e., metallic ribbon) and the fourth segment (i.e., metallic ribbon), the first segment (i.e., metallic ribbon) and the second segment (i.e., metallic ribbon) being maintained in a neutral state. The third segment (i.e., metallic ribbon) and the fourth segment (i.e., metallic ribbon) are charged at an opposite polarity with respect to the charged electrospun fiber. The whipping action characteristic of electrospun fibers causes the fiber to move back and forth the fiber attaching to circumferentially to the third segment (i.e., metallic ribbon) and the fourth segment (i.e., metallic ribbon). The first segment, third segment, intermediate segment, second segment, and fourth segment are collectively rotated by at least one drive motor about a longitudinal axis. Nanofibers attach at multiple points around the perimeter of the third segment (i.e., metallic ribbon) and the fourth segment (i.e., metallic ribbon), spanning the separation space occupied by the intermediate segment. Fibers aligned along the longitudinal axis are held in place on the surface of the electrically grounded intermediate segment during rotation.

Figure 18:
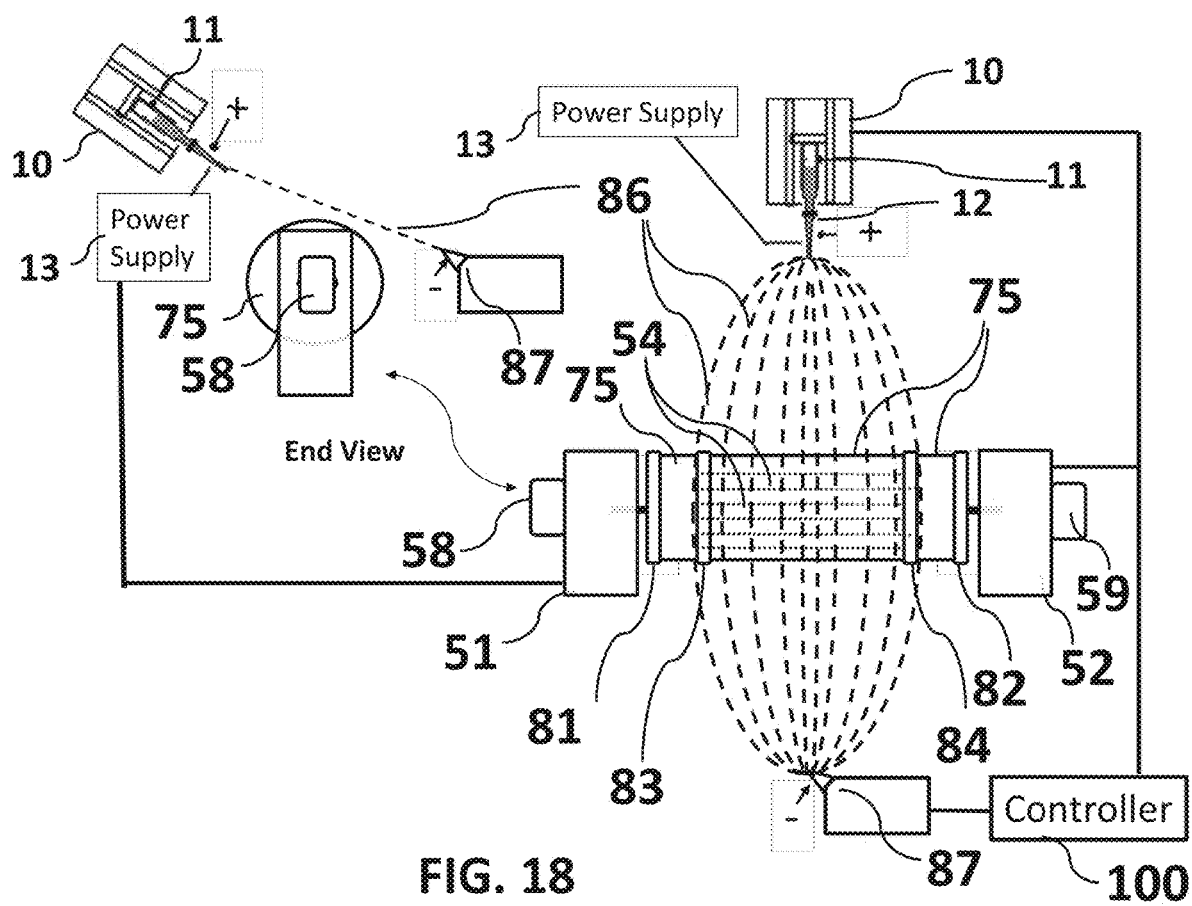
FIG. 18 is a non-limiting diagram showing an embodiment of the present invention installed in an electrospinning device as a fiber collector, where a plurality of nanofibers is attached between a third segment (i.e., metallic ribbon) and a fourth segment (i.e., metallic ribbon), spanning across the length of an intermediate segment (i.e., an elongated cylinder), and a plurality of branched fibers are attracted between a charged emitter and an electrode having an opposing charge, the branched fibers spanning orthogonally across the nanofibers attached to the third and fourth segments.

FIG. 18 is a non-limiting diagram showing an embodiment of the present invention where a plurality of nanofibers is attached between a third segment (i.e., metallic ribbon) and a fourth segment (i.e., metallic ribbon), spanning across the length of an intermediate segment (i.e., an elongated cylinder), and a plurality of branched fibers are attracted between a charged emitter and an electrode having an opposing charge, the branched fibers spanning orthogonally across the nanofibers attached to the third and fourth segments. The emitter is configured for electrospinning nanoscale fiber streams comprising many charged fiber branches, can be electrically charged and has a tip positioned offset away from and between the edge conductor of the third segment (i.e., metallic ribbon) and the edge conductor of the fourth segment (i.e., metallic ribbon). A support structure is provided for rotating the elongated assembly (first segment, second segment, third segment, fourth segment, and intermediate segment) about a longitudinal axis and no electrical charge is applied to the first segment, second segment, third segment, or fourth segment while the steering electrode is electrically charged. An electrically chargeable steering electrode may be provided for attracting the fiber streams along motion pathways substantially orthogonal to motion pathways of fiber streams attracted to the third and fourth segments spanning the intermediate segment. The fibers are attracted to and held at the surface of the intermediate segment between the third and fourth segments when it becomes electrically grounded. Fibers aligned along the longitudinal axis are held in place on the surface of the electrically grounded intermediate segment during rotation.

Figure 19:
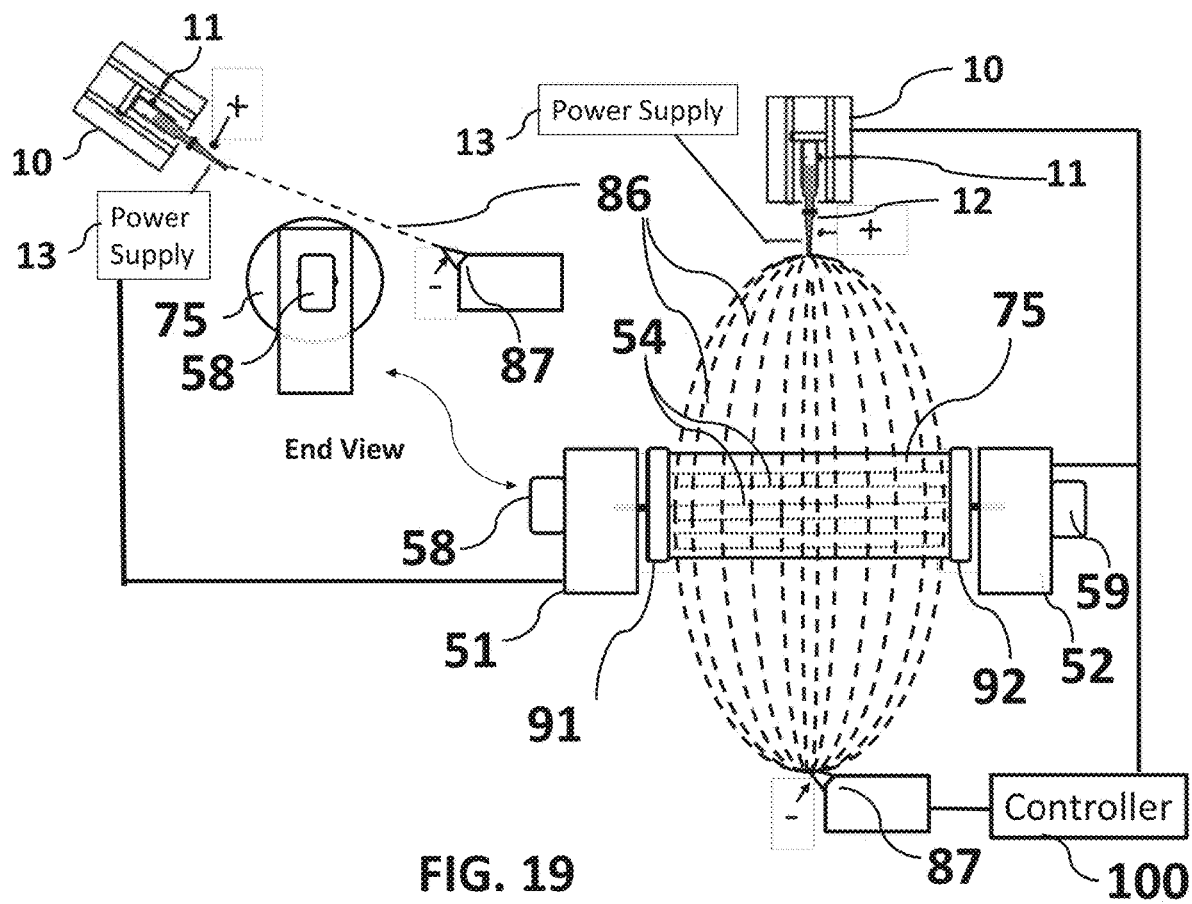
FIG. 19 is a non-limiting diagram showing an embodiment of the present invention installed in an electrospinning device as a fiber collector, where a first segment (i.e., a disk) and a second segment (i.e., a disk), each rotationally mounted on a separate drive motor and moveably separable on a base mount (not shown), are adjustable to accept an intermediate segment (i.e., cylinder) between the first segment and the second segment, and the intermediate segment connects to the first and second segments (i.e., disks) using insulating connectors (not shown).

FIG. 19 is a non-limiting diagram showing an embodiment of the present invention where a first segment (i.e., a disk) and a second segment (i.e., a disk) are shown, each rotationally mounted on a separate drive motor and moveably separable on a base mount, where separation may be adjusted to accept an intermediate segment between the first segment and the second segment (i.e., disks), and the intermediate segment (i.e., cylinder) connects to the first and second segments (i.e., disks) using insulating connectors. The first segment and the second segment are electrically chargeable. The intermediate segment can be charged, maintained electrically neutral, or electrically grounded. The first segment and the second segment may be mounted on separately controllable drive motors that are movably mounted on a base. The span between the first segment and the second segment may be increased to enable mounting the intermediate segment on the insulating connectors. The span may be reduced to secure the intermediate segment in operating position. Intermediate segments of differing lengths may be selected and installed between the first segment and the second segment to produce nanofiber membranes of corresponding width. An electrically chargeable steering electrode may be provided for attracting the fiber streams along motion pathways substantially orthogonal to motion pathways of fiber streams attracted to the first and second segments spanning the intermediate segment. The fibers are attracted to and held at the surface of the intermediate segment between the first and second segments when it becomes electrically grounded. Fibers aligned along the longitudinal axis are held in place on the surface of the electrically grounded intermediate segment during rotation.

Figure 20:
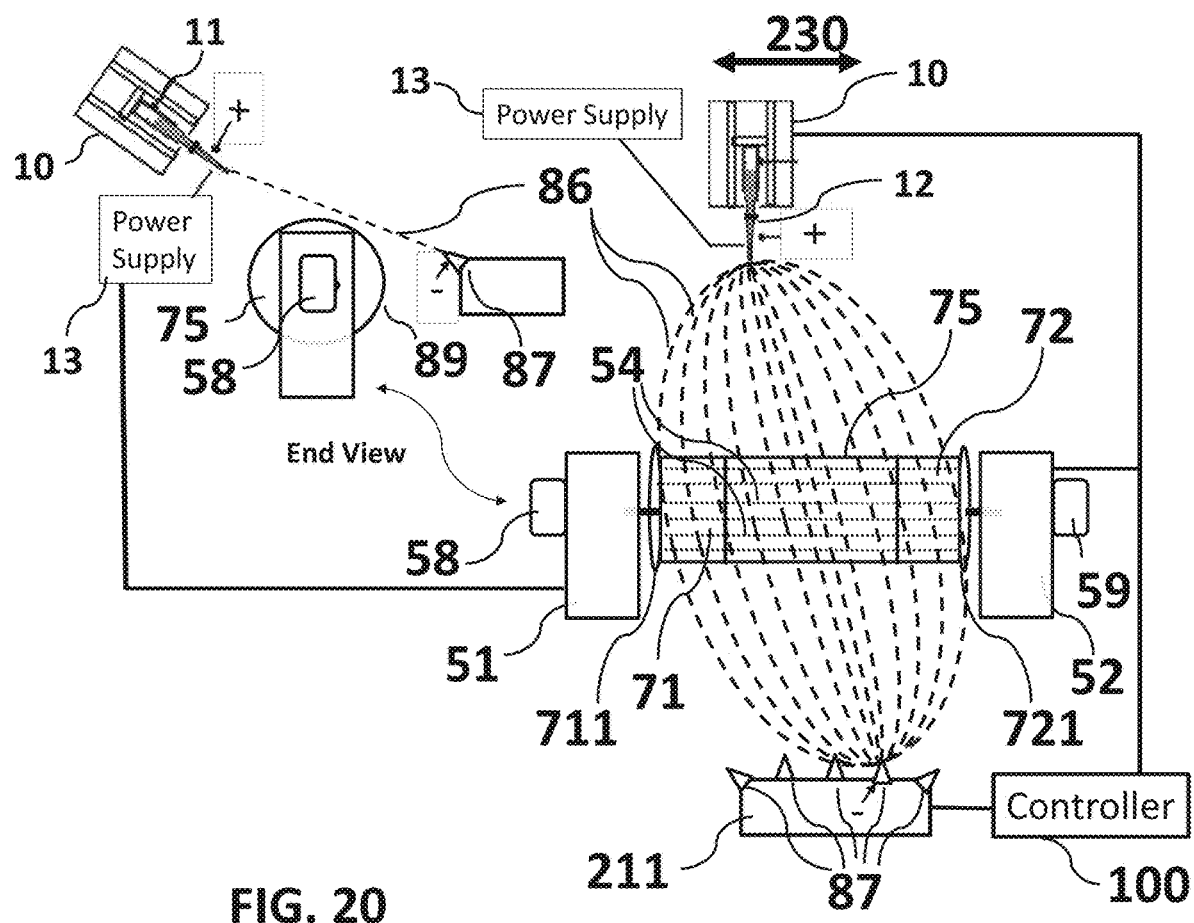
FIG. 20 is a non-limiting diagram showing an embodiment of the present invention installed in an electrospinning device as a fiber collector, where the device is configured with a plurality of steering electrodes.

FIG. 20 is a non-limiting diagram showing an embodiment of the present invention installed in an electrospinning device configured with a plurality of steering electrodes. The steering electrodes may be programably chargeable so that motion pathways of branched fiber streams toward the electrodes from the at least one emitter is alterable. The position of the emitter may also be alterable. A support structure is provided for rotating the elongated assembly (first segment, second segment, and intermediate segment) of the present invention about a longitudinal axis and no electrical charge is applied to the first segment and second segment while a steering electrode is electrically charged. The electrically chargeable steering electrodes are provided for attracting the fiber streams along motion pathways substantially orthogonal or oblique to motion pathways of fiber streams attracted to the first and second segment edge conductors, the fibers spanning the intermediate segment. The fibers are attracted to and held at the surface of the intermediate segment between the first and second segments when it becomes electrically grounded or electrically charged with an opposing charge.

Figure 21:
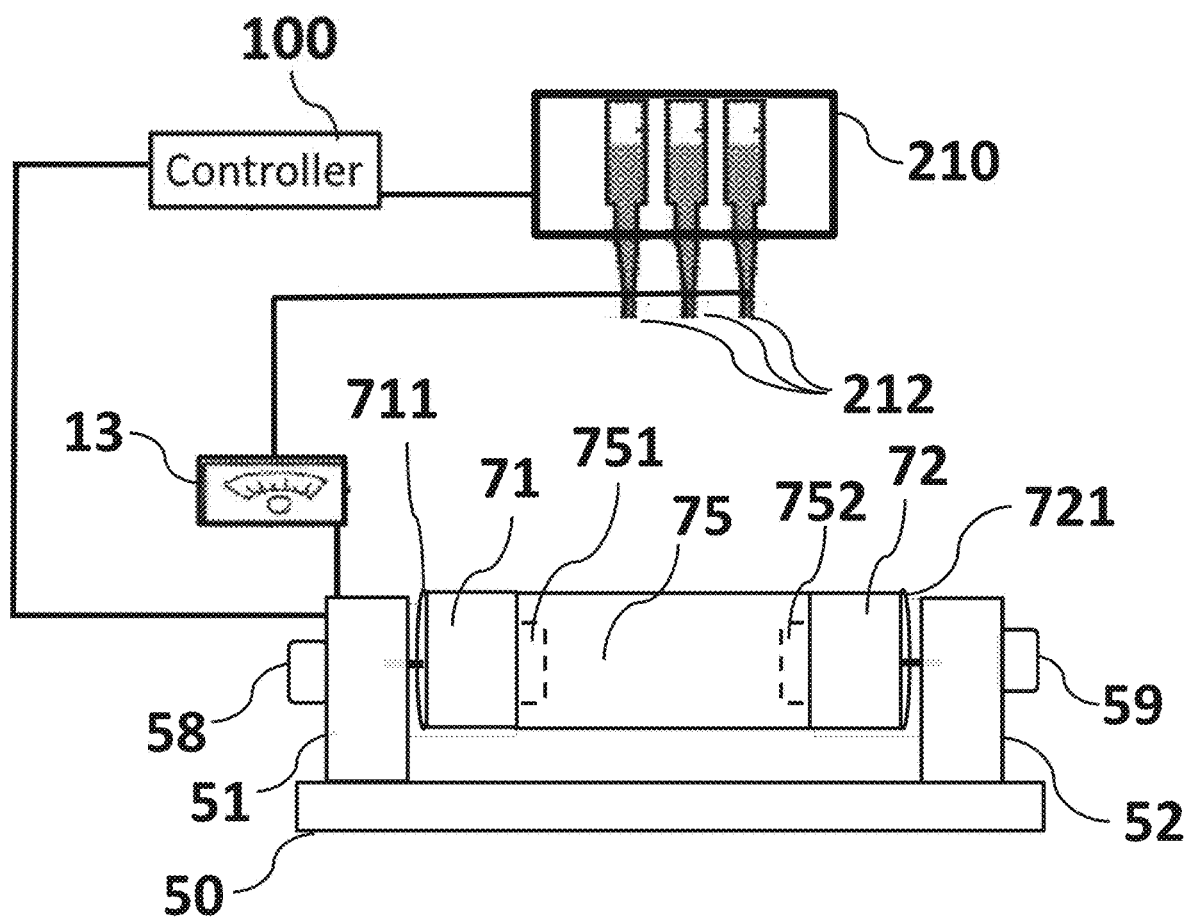
FIG. 21 is a non-limiting diagram showing an embodiment of the present invention installed in an electrospinning device as a fiber collector, where a plurality of emitters is configured in an emitter assembly.

FIG. 21 is a non-limiting diagram showing an embodiment of the present invention installed in an electrospinning device where a plurality of emitters is configured in an emitter assembly. Multiple fiber types, including but not limited to solid, hollow, and core-shell, may be electrospun by configuring the emitter assembly with multiple emitters as shown. The chemical composition of the fibers electrospun from each emitter in the emitter assembly may differ.

Figure 22:
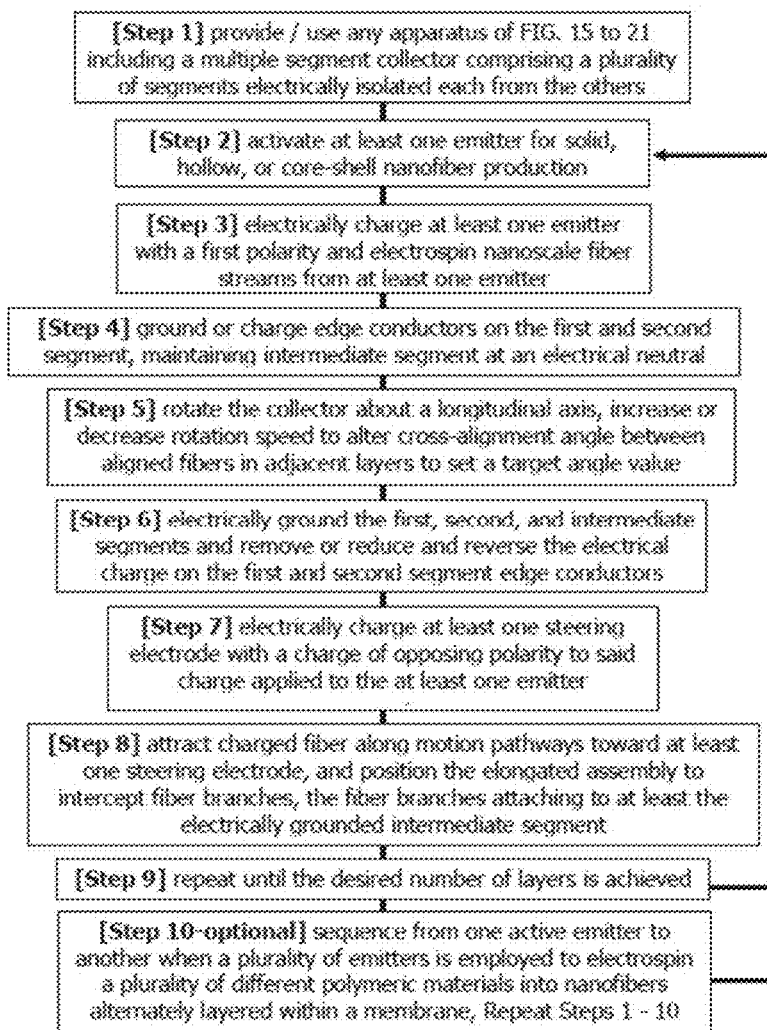
FIG. 22 is a non-limiting diagram presenting a method of the present invention for fabricating a multi-layered, cross-aligned nanofiber membrane usable in constructing at least a layered wound care dressing or biomedical scaffold.

FIG. 22 is a non-limiting image illustrating a method of the present invention for fabricating a cross-aligned nanofiber membrane usable in constructing at least a layered wound care dressing. A preferred embodiment of the present invention comprising at least a first segment, a second segment, and an intermediate segment (i.e., collectively an elongated assembly) is installed in an electrospinning device. Nanoscale fiber streams are electrospun from at least one emitter, the fiber streams comprising many charged fiber branches, the at least one emitter being electrically charged and having a tip positioned offset away from and between the first segment and the second segment. The at least one emitter may be configured to produce any of solid, hollow, or core-shell fibers. A circumferential edge conductor resident on each of the first segment and the second segment is charged by applying a voltage having a first polarity, while maintaining at least the intermediate segment at one of an electrical neutral or electrical ground, the charging imparting a polarity opposing a charge on the at least one emitter realizing an electrical potential difference. The elongated assembly is rotated about a longitudinal axis, and the charged fiber branches are attracted by the opposing electrical charge on a circumferential edge conductor resident on the first segment and on the second segment, where the fibers alternately attach to the circumferential edge conductor of the first segment and the second segment, spanning a separation distance between the edge conductors on the first segment and the second segment. The first, second, and intermediate segments are maintained electrically neutral, and set to electrical ground when the electrical charge is removed from the edge conductor on each of the first segment and the second segment, attracting the fibers attached to the edge conductors. Fibers aligned along the longitudinal axis are held in place on the surface of the electrically grounded intermediate segment during rotation. Cross-aligned fibers are applied to a fiber layer attached to the first, second, and intermediate segments spanning the separation distance between the first segment edge conductor and the second segment edge conductor by rotating the elongated assembly and electrically charging at least one steering electrode with a charge exhibiting an opposing polarity to the charge applied to the at least one emitter producing a charged fiber stream. Branch fibers separate along field lines in the electromagnetic field produced by the opposing electrical charges applied to the at least one emitter and the at least one electrode, and the charged fiber branches attach circumferentially to the first, second, and intermediate segments (i.e., collectively the elongated assembly), the collective segments being electrically grounded.

Figure 23:
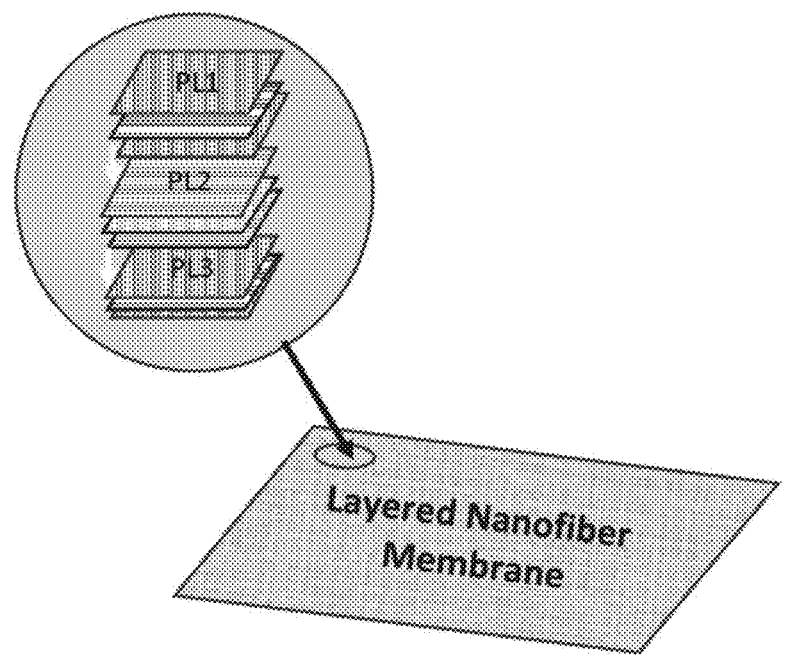
FIG. 23 is a non-limiting diagram presenting a multi-layered nanofiber membrane comprising diverse polymeric materials in each cross-aligned fiber layer that can be fabricated using the method of the present invention, the membrane being usable for delivering active agents in a wound care dressing or biomedical scaffold.

FIG. 23 is a non-limiting diagram presenting a multi-layered nanofiber membrane comprising diverse polymeric materials in each cross-aligned fiber layer that can be fabricated using the method of the present invention, the membrane being usable for delivering active agents in a wound care dressing or biomedical scaffold. The multi-layers as shown are produced when Step 10 is executed in the method of the present invention as presented in FIG. 22.

Figure 24:
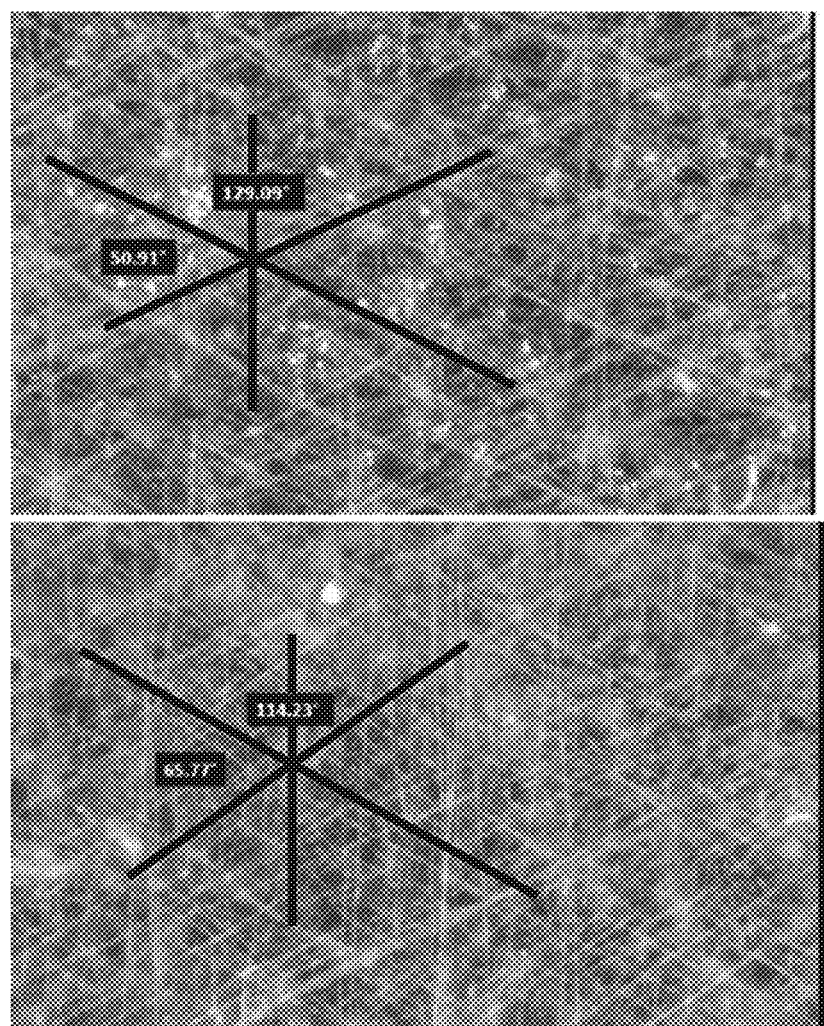
FIG. 24 is a non-limiting diagram showing cross-alignment angles in a plurality of nanofiber membranes where the relative cross-alignment angle between aligned fibers in each fiber layer were altered by increasing or decreasing the rotation speed of the segmented collector.

FIG. 24 is a non-limiting diagram showing cross-alignment angles in a plurality of nanofiber membranes where the relative cross-alignment angle between aligned fibers in each fiber layer were altered using the method of the present invention, the relative angles being altered by increasing or decreasing the rotation speed of the segmented collector. The change in relative angles be between fibers in adjacent fiber layers as shown are produced when Step 5 is executed in the method of the present invention as presented in FIG. 22.

In detail:

Referring now to FIG. 7, a non-limiting diagram shows components of the apparatus of the present invention in a preferred embodiment comprising a first segment 71, a second segment 72, and an intermediate segment 75. The preferred embodiment shown in the diagram includes an electrically chargeable edge conductor 711 circumferentially resident on and electrically insulated from the first segment 71, and an electrically chargeable edge conductor 721 circumferentially resident on and electrically insulated from the second segment 72. The intermediate segment 75 is positioned between the first segment 71 and the second segment 72 to collectively present an elongated cylindrical structure. The first segment 71 and the second segment 72 both are configured with insulated connectors (FIGS. 8, 712 and 722 respectively) for engaging the intermediate segment 75 at 751 and 752 connection points, respectively. The first segment 71 and the second segment 72 both are configured with connection points 755 and 756 for mounting on a drive unit as shown in FIG. 12. The first segment 71, the second segment 72, and the intermediate segment 75 may be electrically grounded or floating. A collector pallet 790 (e.g., medical fabric) may be attached circumferentially around the elongated cylindrical structure on to which pallet fiber is applied in cross-aligned layers. The collector pallet 790 is not removed until the number of desired cross-aligned fiber layers in a membrane is achieved. The membrane (and collector pallet (if used) is removed thereafter. Fiber may be applied in cross-aligned fiber layers directly onto the elongated cylindrical structure absent a collector pallet.

Referring now to FIG. 8, a non-limiting diagram shows components of the apparatus of the present invention in a preferred embodiment comprising a first segment 71, a second segment 72, and an intermediate segment 75, where the first segment and the second segment are disconnected (i.e., separated) from the intermediate segment 75. The preferred embodiment shown in the diagram includes an electrically chargeable edge conductor 711 circumferentially resident on and electrically insulated from the first segment 71, and an electrically chargeable edge conductor 721 circumferentially resident on and electrically insulated from the second segment 72. Connector 712 may connect the first segment 71 to the intermediate segment 75 at one end 751. Connector 722 may connect segment 72 to the intermediate segment 75 at an end 752 opposite the connected first segment 71. The relative positions of the segments configured with edge conductors (711, 721) as shown is not limiting, but may be interchanged. As shown, the first segment 71 and the second segment 72 may be removably connected to the intermediate segment 75 to collectively present an elongated cylindrical structure. The first segment 71 and the second segment 72 both are configured with connection points 755 and 756 for mounting on a drive unit as shown in FIG. 12. The first segment 71, the second segment 72, and the intermediate segment 75 may be electrically grounded or floating (i.e., neutral) when installed and used in an electrospinning device.

Referring now to FIG. 9, a non-limiting diagram shows components of the apparatus of the present invention in a preferred embodiment comprising a first segment 71, a second segment 72, a third segment 73, a fourth segment 74, and an intermediate segment 75, where the first segment 71, the second segment 72, the third segment 73, the fourth segment 74, and the intermediate segment 75 are disconnected (i.e., separated) each from the other. The preferred embodiment shown in the diagram includes electrically chargeable edge conductors (711, 721, 731, 741) circumferentially resident on and electrically insulated from the first segment 71, the second segment 72, the third segment 73, and the fourth segment 74, respectively. As shown, the first segment 71, the second segment 72, the third segment 73, the fourth segment 74, and the intermediate segment 75 may be removably connected to each other to collectively present an elongated cylindrical structure. Connector 712 may connect the first segment 71 to the third segment 73 at end point 733. Connector 732 may connect segment 73 to intermediate segment 75 at one end 751. Connector 722 may connect segment 72 to segment 74 at end point 743. Connector 742 may connect segment 74 to the intermediate segment 75 at an end point 752 opposite the connected third segment 73. Connectors 712, 722, 732, and 742 are electrically insulating connectors. The relative positions of the segments configured with edge conductors (711, 721, 731, 741) as shown is not limiting, but may be interchanged. The first segment 71 and the second segment 72 both are configured with connection points 755 and 756 for mounting on a drive unit as shown in FIG. 12. The first segment 71, the second segment 72, the third segment 73, the fourth segment 74, and the intermediate segment 75 may be electrically grounded or floating (i.e., neutral) when installed in an electrospinning device.

Referring now to FIG. 10, a non-limiting diagram shows components of a preferred embodiment of the present invention configured as a first segment (i.e., metallic ribbon) 81, a second segment (i.e., metallic ribbon) 82, a third segment (i.e., metallic ribbon) 83, and a fourth segment (i.e., metallic ribbon) 84, where the metallic ribbons are and circumferentially mounted on and electrically insulated from the intermediate segment 75, each metallic ribbon being electrically chargeable and presenting an edge. A plurality of nanofibers may be attracted to and attach to either the first segment (i.e., metallic ribbon) 81 and the second segment (i.e., metallic ribbon) 82, or attracted to and attach between the third segment (i.e., metallic ribbon) 83 and the fourth segment (i.e., metallic ribbon) 84, when these respective conductor pairs are electrically charged, the fibers spanning across the length of the intermediate segment (i.e., an elongated cylinder) 75. The intermediate segment 75 is configured with connection points 755 and 756 for mounting on a drive unit as shown in FIG. 17.

Referring now to FIG. 11, a non-limiting diagram shows components of a preferred embodiment of the present invention configured as a first segment (i.e., metallic disk) 91, a second segment (i.e., metallic disk) 92 attachable to an intermediate segment (i.e., an elongated cylinder) 75 at connection points 751 and 752, respectively. Attachment of the first segment 91 and the second segment 92 to the intermediate segment 75 may be accomplished using insulating connectors 911 and 921. A plurality of nanofibers may be attracted to and attach to a circumferential edge on the first segment (i.e., metallic disk) 91 and a circumferential edge on the second segment (i.e., metallic disk) 92, spanning across the length of the intermediate segment (i.e., an elongated cylinder) 75. The first segment 91 and the second segment 92 both are configured with connection points 915 and 925 for mounting on a drive unit as shown in FIG. 13.

Referring now to FIG. 12, a non-limiting diagram shows components of the apparatus of the present invention in a preferred embodiment (FIG. 7) comprising a first segment 71, a second segment 72, and an intermediate segment 75 mounted on a drive unit comprising a base 50, supports 51 and 52, and drive motors 58 and 59. The preferred embodiment shown in the diagram includes an electrically chargeable edge conductor 711 circumferentially resident on and electrically insulated from the first segment 71, and an electrically chargeable edge conductor 721 circumferentially resident on and electrically insulated from the second segment 72. The intermediate segment 75 is positioned between the first segment 71 and the second segment 72 to collectively present an elongated cylindrical structure that can be rotated by the drive unit drive motors 58 and/or 59. The first segment 71 and the second segment 72 both are configured with insulated connectors (FIGS. 8, 712 and 722 respectively) for engaging the intermediate segment 75 at 751 and 752 connection points, respectively. The first segment 71 and the second segment 72 both are configured with connection points (FIGS. 8, 755 and 756) for mounting on a drive unit as shown. The first segment 71, the second segment 72, and the intermediate segment 75 may be electrically grounded or floating (i.e., neutral).

Referring now to FIG. 13, a non-limiting diagram shows a preferred embodiment of the present invention (FIG. 11) installed in an electrospinning device (producing charged fiber 53) such as that disclosed in U.S. patent application Ser. No. 14/734,147. The components of the present invention are shown comprising a plurality of collector segments including at least the first segment 91 (i.e., a disk), a second segment 92 (i.e., a disk), and an intermediate segment 75 (i.e., an elongated cylinder). The first segment 91 is positioned and connected at one end of the intermediate segment 75 and the second segment 92 is positioned and connected at an opposite end of the intermediate segment 75. The intermediate segment 75 connects to the first segment 91 and the second segment 92 using insulating connectors (911 & 921, FIG. 11). The first segment 91 (i.e., a disk) and the second segment 92 (i.e., a disk) are electrically chargeable and present an electrically chargeable, circumferential edge conductor to electrospun nanofibers. The intermediate segment 75 can be maintained electrically neutral or at electrical ground. The first segment 91 and the second segment 92 may be mounted on separately controlled drive motors (58 and 59) that may be movably mounted on a base 50. The span between supports 51 and 52 may be increased to enable mounting the first segment 91, the second segment 92, and the intermediate segment 75 connected together using the insulating connectors (911 & 921, FIG. 11). At least one emitter 12 may be configured for electrospinning nanoscale fiber streams comprising any of solid, hollow, or core-shell fibers. The pump 10 may be configured with one or two reservoirs (FIG. 5) to hold polymer solutions. The at least one emitter 12 can be electrically charged and configured with a tip positioned offset away from and between an edge conductor of the first segment 91 and an edge conductor of the second segment 92. The at least one emitter 12 may be configured to produce solid fibers typical of electrospinning devices (FIG. 1). The at least one emitter 12 may be configured to produce core-shell fibers (FIG. 5). Emitters (a.k.a., spinnerets, needles) for electrospinning coaxial nanofibers (a.k.a., core-shell nanofibers) are commercially available from sources such as ramé-hart instrument co., Succasunna, NJ. Two syringes for pumping polymer solutions may be used, along with a spinneret which typically consists of a pair of capillary tubes, where a smaller one tube is inserted (inner) concentrically inside a larger (outer) capillary to structure in a co-axial configuration (FIG. 5). Each capillary tube is connected to a dedicated reservoir containing solutions independently supplied by a syringe-pump or air pressure system. For example, two syringe pumps (FIGS. 5, 112 and 113) can be used to impulse both solutions provided to a coaxial spinneret (FIG. 5, 111), which presents two inputs. Inside the coaxial spinneret (FIG. 5, 111) both fluids flow into the tip of the device where the injection of one solution into another produces a coaxial stream. The shell fluid drags the inner one at the Taylor cone of the electrospinning jet. Both polymer solutions are connected to a high-voltage source (FIG. 5, 114) and a charge accumulation forms on the surface of the shell solution liquid. The liquid compound meniscus of the shell liquid elongates and stretches as a result of charge-charge repulsion. This forms a conical shape (Taylor cone). The charge accumulation increases to a certain threshold value due to the increased applied potential, at that point a fine jet extends from the cone. Stresses are generated in the shell solution that cause shearing of the core solution via "viscous dragging" and "contact friction." Shearing causes the core liquid to deform into a conical shape and a compound co-axial jet develops at the tip of the cones. Provided the compound cone remains stable, a core is uniformly incorporated into the shell producing a core-shell fiber formation. As the core-shell fiber moves toward a charged conductor (e.g., FIGS. 13, 91 & 92; FIG. 14, 711 & 721), the jet experiences bending instability, producing a back and forth whipping trajectory and the two solvents in the core-shell stream evaporate, and core-sheath nanofibers are formed. A support structure holding drive motors (58 & 59) as part of the base 50 may be provided for rotating the elongated assembly (91,75,92) about a longitudinal axis and applying an electrical charge to at least the first segment 91 and second segment 92.

Referring now to FIG. 14, a non-limiting diagram shows a preferred embodiment of the present invention (shown in FIG. 7) installed in an electrospinning device producing charged fiber 53, where a nanofiber 54 is attached between an electrically charged edge conductor 711 resident on the first segment 71 and electrically charged edge conductor 721 resident on the second segment 72, spanning across the length of the first, second, and intermediate segments 71, 72, & 75 (i.e., an elongated cylinder). Controller 100 governs the charge status of the at least one emitter 12, first segment edge conductor 711, second segment edge conductor 721, and the first, second, and intermediate segments 71, 72, and 75, as well as the polymer flow rate, and rotation speed of the elongated assembly (71, 711, 75, 72, 721). The charged electrospun fiber 54 is attracted to the first segment edge conductor 711 and the second segment edge conductor 721, which are charged at an opposite polarity with respect to the charged fiber 54. The whipping action characteristic of electrospun fibers causes the emitted fiber 53 to move back and forth, the fiber 54 attaching circumferentially to the edge of the first segment edge conductor 711 and the second segment edge conductor 721 as the elongated assembly (71, 711, 75, 72, 721) is rotated, spanning across the first, second, and intermediate segments 71, 72, and 75.

Referring now to FIG. 15, a non-limiting diagram shows a preferred embodiment of the present invention (shown in FIG. 7) installed in an electrospinning device producing charged fiber 53, where a plurality of nanofibers 54 is attached to the circumferential edge conductors 711 and 721, spanning across at least the length of the first segment 71, the second segment 72, and the intermediate segment 75 (i.e., an elongated cylinder). The charged electrospun fiber 53 is attracted to the first segment edge conductor 711 and the second segment edge conductor 721, which are charged at an opposite polarity with respect to the charge applied to the emitter 12 and the charged fiber 53. The emitter 12 is configured for electrospinning nanoscale fiber streams comprising any of solid, hollow or core-shell fibers, can be electrically charged, and has a tip positioned offset away from and between the first segment edge conductor 711 and the second segment edge conductor 721. The whipping action characteristic of electrospun fibers causes the emitted fiber to move back and forth, the fiber 54 attaching circumferentially to the first segment edge conductor 711 and the second segment edge conductor 721 as the elongated assembly is rotated. The first segment 71, the intermediate segment 75, and the second segment 72 are collectively rotated by at least one drive motor (58, 59) about a longitudinal axis. During collective rotation of the segments (71, 72, 75), nanofibers 54 attach at multiple points around the perimeter of the first segment edge conductor 711 and the second segment edge conductor 721, the nanofibers 54 being substantially aligned and spanning at least the separation space occupied by the intermediate segment 75. Electrically grounding the the intermediate segment 75 along with the first segment 71 and the second segment 72 attracts the nanofibers 54 to the surface of each segment. Fibers aligned along the longitudinal axis are held in place on the surface of the electrically grounded intermediate segment during rotation.

Referring now to FIG. 16, a non-limiting diagram shows a preferred embodiment of the present invention (shown in FIG. 7) installed in an electrospinning device, where a plurality of nanofibers 54 is attached between and circumferentially around the first segment edge conductor 711 and the second segment edge conductor 721, substantially aligned and spanning across the length of the first, second, and intermediate segments 71, 72, 75 (i.e., an elongated cylinder). Electrically grounding the the intermediate segment 75 along with the first segment 71 and the second segment 72 attracts and holds the nanofibers 54 on the surface of each segment. A plurality of branched fibers 86 expelled from the emitter 12 is attracted between the charged emitter 12 and a steering electrode 87 having an opposing charge, the branched fibers 86 being substantially aligned and spanning orthogonally across and proximate to the nanofibers 54 that attached to the first segment edge conductor 711 and the second segment edge conductor 721 during rotation, and attracted to the first segment 71, the second segment 72, and intermediate segment 75 when grounded. The emitter 12 is configured for electrospinning nanoscale fiber streams comprising any of solid, hollow or core-shell fibers, can be electrically charged, and has a tip positioned offset away from and between the first segment edge conductor 711 and the second segment edge conductor 721. A support structure is provided for rotating the elongated assembly (first segment 71, second segment 72, and intermediate segment 75) about a longitudinal axis and no electrical charge is applied to the first segment edge conductor 711 and second segment edge conductor 721 while the steering electrode 87 is electrically charged. Fibers 54 aligned along the longitudinal axis are held in place on the surface of the electrically grounded intermediate segment 75 during rotation. The electrically chargeable steering electrode 87 is provided for attracting the fiber streams along motion pathways substantially orthogonal to motion pathways of fiber streams attracted to the first segment edge conductor 711 and second segment edge conductor 721 spanning at least the intermediate segment 75. The fibers 86 are attracted to the surface of the combined first segment 71, the second segment 72, and intermediate segment 75 when each segment becomes electrically grounded, and overlay nanofibers 54 present at the surface of the first segment 71, second segment 72, and the intermediate segment 75. By alternating, during collective rotation of the first segment 71, the second segment 72, and the intermediate segment 75, the application of an opposing charge on the electrode 87 with applying an opposing charge on the first and second segment edge conductors (711 & 721) collectively, multiple layers of nanofibers (54 & 86) can be accumulated, the nanofibers in each layer being substantially aligned, and the aligned fibers in each layer being substantially orthogonal to aligned fibers comprising an adjacent layer. Differing lengths of intermediate segment 75 may be selected and installed between the first segment 71 and the second segment 72 to produce fibrous membranes of correspondingly differing width and comprising cross-aligned nanofibers collected at the surface of the intermediate segment 75 and the first and second segments (71 & 72) using the method and apparatus as taught herein (illustrated in FIG. 22).

Referring now to FIG. 17, a non-limiting diagram shows a preferred embodiment of the present invention (as shown in FIG. 10) installed in an electrospinning device producing charged fiber 53, the embodiment configured with a first segment 81 (i.e., metallic ribbon), a second segment 82 (i.e., metallic ribbon), a third segment 83 (i.e., metallic ribbon), a fourth segment 84 (i.e., metallic ribbon), and an intermediate segment 75, where a plurality of nanofibers 54 is attached to the third segment 83 (i.e., metallic ribbon) and the fourth segment 84 (i.e., metallic ribbon), spanning across the length of the intermediate segment 75 (i.e., an elongated cylinder) between the third and fourth segments (83 & 84). The metallic ribbons (81, 82, 83, 84) are attached to and electrically insulated from the surface of the intermediate segment 75 which extends the full length between the supports 51 and 52, comprising the elongated cylinder. The charged electrospun nanofiber 53 is attracted to the third segment 83 and the fourth segment 84 when electrically charged with a charge opposing the charge on the fibers 53, the first segment 81 and the second segment 82 being maintained in an electrically neutral state. The third segment 83 and the fourth segment 84 are charged at an opposite polarity with respect to the charged emitter 12 and electrospun fiber 53. The whipping action characteristic of electrospun fibers causes the emitted fiber to move back and forth, the expelled fiber 53 attaching circumferentially as attached fiber 54 to the third segment 83 and the fourth segment 84. The first segment 81, third segment 83, intermediate segment 75, second segment 83, and fourth segment 84 are collectively rotated by at least one drive motor (58, 59) about a longitudinal axis. Nanofibers 54 attach at multiple points around the perimeter of the third segment 83 and the fourth segment 84, spanning the separation space occupied by the intermediate segment 75 between the third and fourth segments (83 & 84), the fibers 54 being substantially aligned. Electrically grounding the the intermediate segment 75 attracts the nanofibers 54 to the surface of the intermediate segment 75 and holds the fibers between the third and fourth segments (83 & 84). The length of nanofibers 54 collected may be altered by selecting collectively and applying a charge either to the first and second segments (81 & 82) or the third and fourth segments (83 & 84). Charging the first and second segments (81 & 82) will cause longer fibers to be collected compared to collecting fibers between charged third and fourth segments (83 & 84).

Referring now to FIG. 18, a non-limiting diagram shows a preferred embodiment of the present invention (FIG. 10) installed in an electrospinning device, where a plurality of nanofibers 54 is attached to the third segment 83 (i.e., metallic ribbon) and the fourth segment 84 (i.e., metallic ribbon), spanning across the length of the intermediate segment 75 (i.e., an elongated cylinder) between the third and fourth segments (83 & 84). Fibers 54 aligned along the longitudinal axis are held in place on the surface of the electrically grounded intermediate segment 75 during rotation. A plurality of branched nanofibers 86 is attracted between a charged emitter 12 and an electrode 87 having an opposing charge, the branched nanofibers 86 substantially aligned and spanning substantially orthogonally across the nanofibers 54 attached to the third and fourth segments (83 & 84). The emitter 12 is configured for electrospinning nanoscale fiber streams comprising many charged fiber branches 86, can be electrically charged and has a tip positioned offset away from and between the edge conductor of the third segment 83 and the edge conductor of the fourth segment 84. A support structure is provided for rotating the elongated assembly (first segment 81, second segment 82, third segment 83, fourth segment 84, and intermediate segment 75) about a longitudinal axis and no electrical charge is applied to the first segment 81, second segment 82, third segment 83, or fourth segment 84 while the steering electrode 87 is electrically charged. The electrically chargeable steering electrode 87 is provided for attracting fiber streams (collectively 86) along motion pathways substantially orthogonal to motion pathways of fibers (collectively 54) attracted to the third and fourth segments (83 & 84) spanning the intermediate segment 75 between those segments (83 & 84). The fibers (collectively 54) are attracted to the surface of the intermediate segment 75 between the third and fourth segments (84 & 85) as it is electrically grounded when the electrode 87 is electrically charged. The length of nanofibers 54 collected may be altered by selecting collectively for applying a charge either the first and second segments (81 & 82) or the third and fourth segments (84 & 85). Charging the first and second segments (82 & 83) will cause longer fibers to be collected than collecting fibers between charged third and fourth segments (83 & 84). Concurrently electrically grounding the intermediate segment 75 only in the span between charged third and fourth segments (83 & 84) will result in a cross-alignment of nanofibers having a narrower width than charging the first and second segments (81 & 82) while grounding the intermediate segment 75 and third and fourth segments (83 & 84) collectively. The emitter 12 is configured for electrospinning nanoscale fiber streams comprising any of solid, hollow or core-shell fibers.

Referring now to FIG. 19, a non-limiting diagram shows a preferred embodiment of the present invention (as shown in FIG. 11) installed in an electrospinning device, where the first segment 91 (i.e., a disk) and the second segment 92 (i.e., a disk), each rotationally mounted to a separate drive motor (58, 59) and moveably separable on a base mount 50 adjustable to accept the intermediate segment 75 between the first segment 91 and the second segment 92 (i.e., disks). The intermediate segment 75 (i.e., cylinder) connects to the first segment 91 and the second segment 92 (i.e., disks) at connection points 751 and 752 as shown in FIG. 11 using insulating connectors 911 and 921 as shown in FIG. 11. The first segment 91 and the second segment 92 are electrically chargeable. The intermediate segment 75 can be maintained electrically neutral or at electrical ground. Fibers 54 aligned along the longitudinal axis are held in place on the surface of the electrically grounded intermediate segment 75 during rotation. The first segment 91 and the second segment 92 are mounted on separately controllable drive motors (58 & 59) that are movably mounted on the base mount 50. The span between the first segment 91 and the second segment 92 may be increased to enable connecting the intermediate segment 75 to the insulating connectors 911 and 921 (FIG. 11). The insulating connectors 911 and 921 may be configured to insert into receiving ports 751 and 752 respectively. The span is reduced to secure the intermediate segment 75 in operating position. Intermediate segments of differing lengths may be selected and installed between the first segment 91 and the second segment 92 to produce fibrous membranes of corresponding width and comprising cross-aligned nanofibers collected at the surface of the intermediate segment 75 using the method and apparatus as taught herein (see FIG. 22). Attaching a collector pallet (e.g., medical fabric, FIG. 7, 790) to the intermediate segment 75 prior to initiating electrospinning operation will collect nanofibers 54 and 86 on its surface and enable a method of harvesting cross-aligned fiber membranes after a desired layer count of cross-aligned fibers is achieved and electrospinning operation is completed. There are no intervening manual steps in the method of using preferred embodiments of the present invention to create multi-layered fiber membranes in an electrospinning device. There is no need to remove the collector pallet (FIG. 7, 790) until the desired number of fiber layers is achieved.

FIG. 20 is a non-limiting image showing a preferred embodiment of the present invention (as shown in FIG. 7) installed in an electrospinning device configured with a plurality of steering electrodes 87. The steering electrodes 87 may be programably chargeable so that motion pathways of branched fiber streams (collectively 86) toward the electrodes 87 from the at least one emitter 12 is alterable. Motion pathways may be moved off-center by charging an electrode 87 positioned off-center. The position of the emitter 12 may also be alterable with respect to the elongated assembly (71, 72, 75) and the electrodes 87. Repositioning the electrodes 87 or the emitter 12 will alter the cross-alignment of fibers (collectively 86) to an oblique angle with respect to the fibers 54 collected between the charged edge conductors 71 and 72 on the first and second segments, respectively. Fibers 54 aligned along the longitudinal axis are held in place on the surface of the electrically grounded intermediate segment 75 during rotation.

FIG. 21 is a non-limiting image showing a preferred embodiment of the present invention (as shown in FIG. 7) installed in an electrospinning device where a plurality of emitters 212 is configured in an emitter assembly 210. Multiple fiber types, including but not limited to solid, hollow, and core-shell, may be electrospun by configuring the emitter assembly 210 with multiple emitters 212 as shown. The chemical composition of the fibers electrospun from each emitter 212 in the emitter assembly 210 may differ.

Referring now to FIG. 22, a non-limiting diagram shows a method of using a preferred embodiment of the present invention (as shown in FIGS. 7 & 8) in an electrospinning device configured as shown in FIGS. 15, 16, and 20 for fabricating cross-aligned nanofiber membranes usable in constructing multi-layered nanofiber fiber membranes. The method may also be implemented in an electrospinning device using the preferred embodiments of the present invention shown in FIGS. 9, 10, & 11. Cross-aligned nanofiber membranes produced using the apparatus of the present invention are usable at least in constructing a nanofiber matrix usable in a plurality of biomedical applications including an extra cellular matrix for tissue engineering and a layered nanofiber membrane for wound care. The steps of the method comprise:

[Step 1] rotating in an electrospinning device a multiple segment collector, the collector configured with a plurality of segments comprising at least a first segment, a second segment, and an intermediate segment, the first and second segments each including an electrically chargeable, circumferential edge conductor;

[Step 2] activating an emitter for solid, hollow or core-shell fiber production;

[Step 3] electrospining nanofiber streams from at least one emitter 12 as shown in FIG. 15 through 21), the at least one emitter 12 being electrically charged and having a tip positioned offset away from and between electrically chargeable circumferential edge conductors of a first segment 71 and a second segment 72 as shown on FIGS. 15 and 16;

[Step 4] electrically grounding or applying a voltage having a first polarity charging the first segment edge conductor 711 and the second segment edge conductor 721, while maintaining at least the intermediate segment 75 (FIGS. 15 and 16) at one of an electrical neutral or electrical ground, the charging imparting a polarity opposing a charge on the at least one emitter 12 (FIGS. 15 and 16) realizing an electrical potential difference;

[Step 5] increasing or decreasing the rotation speed of the elongated assembly about a longitudinal axis to alter the angular cross-alignment relationship between aligned nanofibers in adjacent layers, rotating the multiple segment collector, collectively the first segment 71, second segment 72, intermediate segment 75 (FIGS. 15 and 16) about a longitudinal axis, the charged fiber 53 being attracted by the grounded or the opposing electrical charge on a circumferential edge conductor 711 resident on the first segment 71 and a circumferential edge conductor 721 resident on the second segment 72, the fibers 54 alternately attaching to the circumferential edge conductor 711 of the first segment 71 and the circumferential edge conductor 721 of second segment 72, spanning a separation distance occupied by the first, second, and intermediate segments (71, 72, 75, FIG. 15) between the first segment edge conductor 711 and the second segment edge conductor 721;

[Step 6] setting the first, second, and intermediate segments (71, 72, 75, FIG. 15) to electrical ground and altering charge level, polarity, or removing the electrical charge from the first segment edge conductor 711, FIG. 15 and the second segment edge conductor 721, FIG. 15, to attract the fibers 54 spanning the edge conductor (711, 721) separation distance to the surface of the multiple segment collector (71, 72, 75);

[Step 7] electrically charging at least one steering electrode 87, FIG. 16 with a charge exhibiting an opposing polarity to the charge applied to the at least one emitter 12 producing a charged fiber stream (collectively 86) separated along field lines in the electromagnetic field produced by the opposing electrical charges applied to the at least one emitter (12, FIG. 16) and the at least one electrode (87, FIG. 16);

[Step 8] attracting charged nanofibers (86, FIG. 16) to the surface of the multiple segment collector comprising first, second, and intermediate segments (71, 72, 75, FIG. 16) and overlay nanofibers (54, FIG. 16) present at the surface of the multiple segment collector (71, 72, 75), collectively rotate the multiple segment collector (71, 72, 75), attracting the charged nanofiber branches 86 along motion pathways toward the at least one steering electrode 87 and attach circumferentially to the multiple segment collector (71, 72, 75), the first, second, and intermediate segment (71, 72, 75, FIG. 16) being electrically grounded and positioned in line-of-sight of the nanofibers 86 to collect nanofibers (86, FIG. 16) cross-aligned over a nanofiber layer (54, FIG. 16) attached at the surface of the first, second, and intermediate segments (71, 72, 75 as shown in FIG. 16), rotating the elongated assembly (71, 72, 75);

[Step 9] electrospining fiber, while alternating from time to time (e.g. 60 second periods) the application of an opposing charge on the electrode (87, FIG. 16) with applying an opposing charge on the first and second segments (71 & 72, FIG. 16) collectively, accumulated multiple layers of nanofibers (54, 86, FIG. 16) until a desired number of layers (e.g., 18 to 24 layers, more or less depending on membrane intended use) is achieved, the collected fibers in each layer being substantially aligned and substantially orthogonal to collected fibers comprising an adjacent layer.

[Step 10—optional] sequence from one active emitter to another when a plurality of emitters is employed to electrospin a plurality of different polymeric materials into nanofibers alternately layered within a membrane, then repeat Steps 1 through 10 until the desired number of fiber layers is achieved, each layer comprising the polymeric material selected.

The preferred embodiments (FIG. 7 through 11) of present invention as shown installed in non-limiting diagrams of FIG. 12 through 21 may collect core-shell nanofiber discharged from at least one coaxial emitter 12 (i.e., spinneret). In a preferred embodiment, the method for collecting fiber threads, comprises providing an electrospinning device configured at least as shown in any of FIG. 13 through 21. By way of example, the electrospinning device may include at least the elongated assembly (71, 72, 75, FIG. 16) having a plurality of segments consisting of at least a first segment 71, a second segment 72, and an intermediate segment 75, the first segment 71 positioned and attached at one end of the intermediate segment 75 and the second segment 72 positioned and attached at an opposite end of the intermediate segment 75. Nanoscale core-shell fiber streams 83 are electrospun from at least one coaxial emitter 12, the fiber streams 83 comprising many charged fiber branches, the at least one coaxial emitter 12 being electrically charged and having a tip positioned offset away from and between the first segment edge conductor 711 and the second segment edge conductor 721. The first segment 71 and the second segment 72 are charged by applying a voltage having a first polarity, while maintaining at least the intermediate segment 75 at one of an electrical neutral or electrical ground, the charging of the edge conductor (711, 721) resident on segments 71 and 72 imparting a polarity opposing a charge on the at least one coaxial emitter 12, realizing an electrical potential difference. The multiple segment collector (71, 72, 75) comprising at least three segments (71, 72, 75) is rotated about a longitudinal axis, and the charged fiber branches 53 are attracted by the opposing electrical charge on a circumferential edge conductor 711 of the first segment 71 and the circumferential edge conductor 721 of the second segment 72, longitudinally spanning at least the intermediate segment 75. The back and forth whipping motion typical of fibers produced by electrospinning presents fiber branches toward the electrically chargeable edge conductors (711, 721) of the elongated assembly (71, 72, 75) where the fibers 54 alternately attach to the circumferential edge conductors (71, 72) of the first and second segments (71, 72), spanning a separation distance between the first segment edge conductor 711 and the second segment edge conductor 721. The first segment 71, the second segment 72, and the intermediate segment 75 are maintained electrically neutral during fiber 54 collection on the circumferential edge conductors (711, 721) of the first segment 71 and the second segment 72, and set to electrical ground when the electrical charge is removed from the first segment edge conductor 711 and the second segment edge conductor 721. Grounding the first segment 71, the second segment 72, and the intermediate segment 75 attracts and holds the charged core-shell fibers 54 that span the separation distance between the first segment edge conductor 711 and the second segment edge conductor 721 to the collective surface (71, 72, 75), the collective surface supporting the fibers 54 during rotation of the intermediate segment 75. Attraction of fibers 54 to the collective surface (71, 72, 75) may also be accomplished by applying a charge to the first segment 71, the second segment 72, and the intermediate segment 75, the charge having a polarity opposing the charge present on the fibers 54. Cross-aligned core-shell fibers are collected over a previously collected fiber layer present on the collective surface (71, 72, 73) spanning the separation distance between the first segment edge conductor 711 and the second segment edge conductor 721 by rotating the elongated assembly (71, 72, 75) and electrically charging at least one steering electrode 87 with a charge exhibiting an opposing polarity to the charge applied to the at least one coaxial emitter 12 producing a charged core-shell fiber stream 86. Core-shell fibers 86 separate along field lines in the electromagnetic field produced by the opposing electrical charges applied to the at least one coaxial emitter 12 and the at least one electrode 87. Charged fibers 86 are attracted along motion pathways from the at least one coaxial emitter 12 toward the at least one steering electrode 87. The elongated assembly (71, 72, 75) is positioned (line-of-sight) to intercept the core-shell fiber 86, and the charged fibers 86 attach circumferentially to the collective surface of segments 71, 72, and 75, the collective surface (71, 72, 75) being electrically grounded or having a charge opposing the charge present on the fibers 86. The emitter assembly 10 may be adjustably positioned to alter the angle at which core-shell fibers 86 expelled from the at least one emitter 12 cross the rotating elongated assembly (71, 72, 75). Similarly, the steering electrode 87 or a steering electrode assembly (FIG. 20-211) may be programed or adjustably positioned to alter the angle at which fibers 86 expelled from the at least one emitter 12 cross the rotating elongated assembly (71, 72, 75).

A collector pallet (790, FIG. 7) in the form of (for example) a film, medical fabric, or porous material may be attached circumferentially and collectively around the first segment 71, the second segment 72, and the intermediate segment 75 of the elongated assembly (71, 72, 75) positioned between the electrically chargeable edge conductors (711 & 721) resident on the first segment 71 and the second segment 72. The charged fiber branches 54 in the core-shell fiber streams attach to the surface of the collector pallet (790, FIG. 7) between the charged edge conductors (711, 721) of first and second segments (71 & 72) across the separation distance when the charge is removed from the edge conductors (711, 721) of the first and second segments (71 & 72) and the collective surface of the first segment 71, the second segment 72, and the intermediary segment 75 is electrically grounded or electrically charged with an opposing charge. The charged core-shell fiber streams 86 attach to the collector pallet (790, FIG. 7) between the electrically neutral edge conductors (711, 721) of the first and second segments (71 & 72) around the circumference of the electrically grounded or charged collective surface (71, 72, 75) when the charged core-shell fiber streams 86 assume a motion pathway toward the at least one electrically charged electrode 87 and are intercepted by the rotating multiple segment collector (71, 72, 75). Repeating the forgoing process results in a fiber membrane comprising core-shell nanofiber layers, where the fibers 86 in each layer of fibers 86 are substantially orthogonal to the fibers 54 in each adjacent layer of fibers 54.

In some embodiments, the at least one steering electrode 87 (e.g. as shown in FIGS. 16 and 18) may be movably mounted on a robotic arm assembly (not shown) for repositioning with respect to the emitter 12 and the multiple segment collector (81, 82, 83, 84, FIG. 18). Repositioning the at least one electrode 87 alters the motion pathway of fibers 86 during electrospinning and may be used to apply fibers 86 in one layer on the multiple segment collector (81, 82, 83, 84, FIG. 18) at oblique angles to fibers 54 applied in a previously applied layer. In some embodiments, a plurality of electrodes 87 (e.g. FIG. 20) may also be mounted on a robotic arm assembly (not shown) or they may be fixedly mounted on a base (211, FIG. 20). By controlling the level of charge applied to each steering electrode 87 in a plurality of steering electrodes (FIG. 20) and the sequencing in which the charging is applied, the motion pathways of the charged fiber branches 86 toward the plurality of steering electrodes 87 mounted on the base (211, FIG. 18) can be altered and fiber application on to multiple segment collector (81, 82, 83, 84, FIG. 18) can be controlled. In some embodiments, the first and second segments (81 & 82) may also be electrically grounded along with the intermediate segment 75 depending upon the operating requirements for the material being electrospun. A collector pallet (790, FIG. 7) affixed circumferentially around at least the intermediate segment 75 of the multiple segment collector (81, 82, 83, 84) may comprise one of a biomedical textile or a wound dressing medical fabric, and single or a plurality of textile or fabric layers may be used to construct a pallet. A layered drug delivery dressing can be fabricated using the present method and apparatus, combining nanofibers formulated for drug release with biomedical textile or other type of wound dressing fabric, and further assembled using components typical of medical dressings, such as a coagulant and absorbents. Multiple fiber types, including but not limited to solid and core-shell, may be electrospun by configuring the emitter assembly (210, FIG. 21) with multiple emitters (212, FIG. 21) as shown in FIG. 21. The chemical composition of the fibers electrospun from each emitter in the emitter assembly (210, FIG. 21) may differ. A resultant fiber membrane may include tissue growth stimulants, the fiber membrane providing for example a three-dimensional (3D) scaffold or an extracellular matrix (ECM) to support tissue regeneration.

In some embodiments, the present invention as shown installed in non-limiting diagrams of FIG. 12 through 21 may collect core-shell nanofiber discharged from at least one emitter 12 (i.e., spinneret). Both synthetic and natural polymers can be used in the methods of the present invention to develop core-shell nanofiber membranes exhibiting targeted physiochemical and biological properties. Non-limiting examples include the polymeric materials poly (lactic-co-glycolic acid) (PLGA), polyvinylpyrrolidone (PVP), polyurethane (PU), poly(ethyleneoxide) (PEO), PVP/cyclodextrin, polyvinyl alcohol (PVA), polycaprolactone (PCL), polyethylene glycol (PEG), PVP/ethyl cellulose, PVP/zein, Cellulose acetate, Eudragit L, hydroxypropyl methylcellulose (HPMC) and analogues thereof. Various combinations of these and other polymeric materials and compounds may be used to produce fiber membranes in accordance with the methods of the present invention. In a preferred embodiment, the method for collecting fiber threads (FIG. 22), comprises providing an electrospinning device configured at least as shown in any of FIG. 13 through 21 with a plurality of emitters (FIG. 21) to produce a multifunction membrane comprising at least one of solid, hollow, and core-shell, cross-aligned nanofiber structures. The multifunction membrane produced using the methods of the present invention (FIG. 22) can provide a matrix for delivering anti-microbial agents, hemostatic agents, analgesics, and a selectable range of therapeutic agents including, but not limited to regenerative agents. The multifunction membrane may be structured as a single, multilayer membrane as shown in the non-limiting diagram of FIG. 23. The membrane may comprise at least three primary layers of nanofibers: a first primary layer (PL1), a second primary layer (PL2), and a third primary layer (PL3) where the second primary layer (PL2) is positioned between the first and third primary layer, and each primary layer comprises at least multiple sublayers of cross-aligned core-shell nanofibers. The nanofibers in the first (PL1) and third (PL3) primary layers may comprise a first polymeric material capable of retaining an agent of interest (e.g. antimicrobial, analgesic) and releasing the agent of interest over tunable time periods in response to specific biological stimulants (e.g., responsive to bacteria, emersion in human blood). An antimicrobial agent such as, but not limited to hypochlorous acid (HClO), polyhexamethylene biguanide (PHMB), or an Essential Oil (e.g., cinnamon EO, oregano EO) infused into polymeric material may be delivered as a burst release from the shell of a core-shell fiber over a short time period (e.g., 2-hour) and delivered as a progressive release from the core of the core-shell fiber over an extended time period (e.g., 72-hour period). The polymeric material comprising the third primary layer may differ from the polymeric material of the first primary layer for some applications. The nanofibers in the second (PL2) primary layer may comprise a second polymeric material capable of delivering at least one of analgesics (e.g., Lidocaine or Bupivacaine) and regenerative agents such as pharmaconutrients, arginine and the omega-3 polyunsaturated fatty acids, and endogenous platelet derived growth factor (PDGF). Hemostatic agents (e.g., fibrinogen/thrombin or polysaccharide particles) may be impregnated into the non-woven nanofiber fabric comprising the membrane, infused into the polymeric material in a fiber layer prior to electrospinning, or applied as coatings on the fiber in the membrane. Additional primary layers (e.g., fourth and fifth) may encapsulate different agent classes relative to agents encapsulated in the first, second, and third primary layers. Added primary layers (e.g., fourth and fifth) may comprise any of immune modulators (e.g., calcineurin inhibitors, antimetabolites, alkylating agents), oxygenating agents (e.g., supersaturated oxygen suspension using perfluorocarbon components) and pH stabilizers (e.g., hyaluronic acid). Alternating electrospun nanofiber layers in the cross-aligned structure of the multifunction membrane enables sequencing of agent release and variation of release profile for the agent of interest. The nanofibers in added primary layers may comprise multiple material compositions in adjacent layers to facilitate delivery of various agent classes to a trauma wound. The materials selected may have differing release profiles depending on delivery sequencing (e.g., hemostatic, antibacterial, analgesic, regenerative agents, immune modulators, oxygenating agents and pH stabilizers). Release can be initiated when multifunction membranes are packed into a trauma wound and exposed to human body fluids (e.g., blood), delivering at least hemostatic, antimicrobial, and analgesic agents into traumatized wound tissue. The multifunction membranes produced using the methods and apparatus of the present invention can be varied in size by altering the dimensions of the segmented collector, and may provide single membrane use for wound packing with multiple membranes as needed.

Referring to FIG. 24, a non-limiting diagram shows cross-alignment angles in two nanofiber membranes where the relative cross-alignment angle between aligned fibers in each fiber layer were altered by increasing or decreasing the rotation speed of the segmented collector. The change in relative angles between fibers in adjacent fiber layers as shown are produced when Step 5 is executed in the method of the present invention as presented in FIG. 22. Increasing or decreasing the rotation speed of the elongated assembly about a longitudinal axis was unexpectedly found to alter the angular cross-alignment relationship between aligned nanofibers in adjacent layers, when rotating the multiple segment collector, collectively the first segment 71, second segment 72, intermediate segment 75 (FIGS. 15 and 16) about a longitudinal axis. Referring to FIG. 15 and FIG. 16, the charged fiber 53 is attracted by the grounded or the opposing electrical charge on a circumferential edge conductor 711 resident on the first segment 71 and a circumferential edge conductor 721 resident on the second segment 72, the fibers 54 alternately attaching to the circumferential edge conductor 711 of the first segment 71 and the circumferential edge conductor 721 of second segment 72, spanning a separation distance occupied by the first, second, and intermediate segments (71, 72, 75, FIG. 15) between the first segment edge conductor 711 and the second segment edge conductor 721. The fibers in each fiber layer are substantially aligned and generally oriented along an alternating direction relative to fibers in adjacent layers exhibiting two distinct radials. Fibers oriented along a third radial are accumulated circumferentially around the segmented collector when the first segment, second segment and third segment are grounded or electrically charged at a polarity opposing the charge on the emitter.

Figure 25:
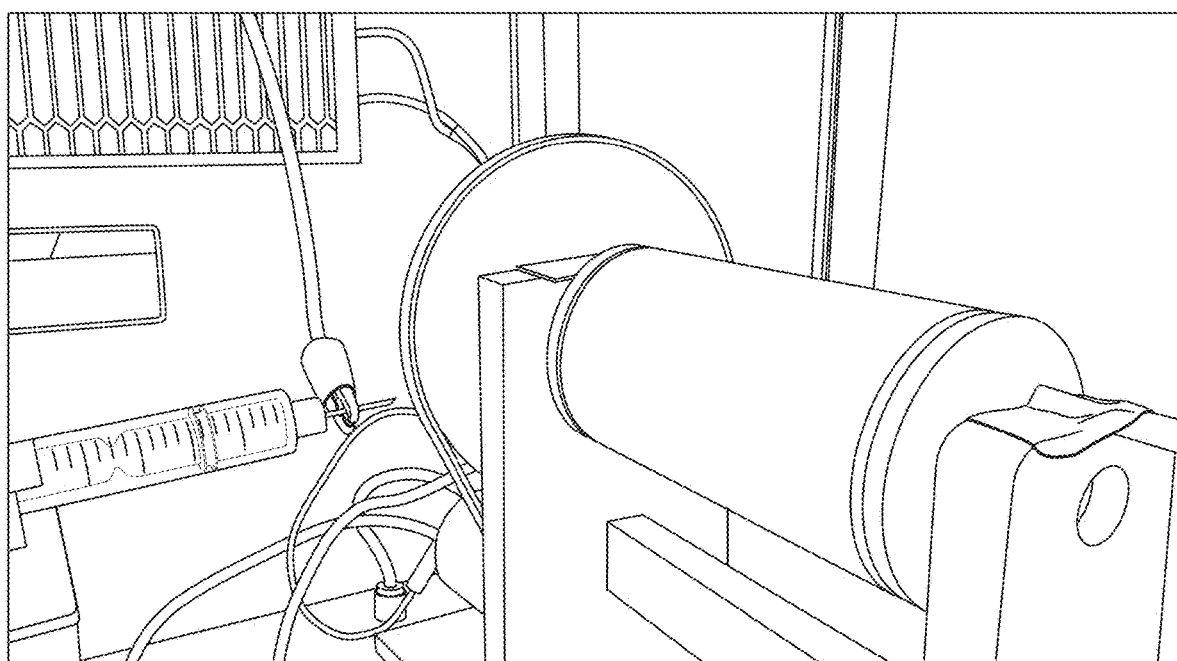
FIG. 25, is a non-limiting diagram showing a prototype of the segmented collector installed in a commercially available laboratory scale electrospinning machine.

Referring to FIG. 25, a prototype of the segmented collector is shown installed in a commercially available laboratory scale electrospinning machine.

EXAMPLES

The present disclosure can be better understood with reference to the following non-limiting examples.

Nanofiber scaffolding structures and aligned fibers produced using the apparatus and methods of the present invention have applications in medicine, including at least artificial organ components, tissue engineering, implant material, drug delivery, wound diagnostics, bacterial detection, wound dressing, and medical textile materials. Nanofiber scaffolding structures may be used to fight against viral infection (e.g., HIV-1, SARS-2), and be able to be used as a contraceptive. In wound healing, nanofiber scaffolding structures assemble at the injury site and stay put, drawing the body's own growth factors to the injury site. These growth factors comprise naturally occurring substances such as proteins and steroid hormones capable of stimulating cellular growth, proliferation, healing, and cellular differentiation. Growth factors are important for regulating a variety of cellular processes. By controlling scaffold structure, relative fiber alignment between fiber layers, fiber membrane porosity, growth factors comprising larger dimension cells can be retained at the wound site to promote healing, while allowing exudate comprising smaller cell fluids to pass through. Scaffolding structures produced by the present invention and methods may be also used to deliver medication to a wound site.

Protective materials incorporating nanofibers produced using the present invention and methods may include sound absorption materials, protective clothing directed against chemical and biological warfare agents, and sensor applications for detecting chemical and biological agents. Gloves incorporating aligned fibers and scaffolding structures produced using the apparatus and methods of the present invention may be configured to provide persistent antibacterial properties. Applications in the textile industry include sport apparel, sport shoes, climbing, rainwear, outerwear garments, and baby-diapers. Napkins and wipes with nanofibers may contain antibodies against numerous biohazards and chemicals that signal by changing color (potentially useful in identifying bacteria in kitchens).

Filtration system applications include HVAC system filters, ULPA filters, air, oil, fuel filters for automotive, trucking, and aircraft uses, as well as filters for beverage, pharmacy, medical applications. Applications include filter media for new air and liquid filtration applications, such as vacuum cleaners. Scaffolding structures produced using the apparatus and methods of the present invention enable high-efficiency particulate arrestance or HEPA type of air filters, and may be used in re-breathing devices enabling recycling of air. Filters meeting the HEPA standard have many applications, including use in personal protective equipment, medical facilities, automobiles, aircraft and homes. The filter must satisfy certain standards of efficiency such as those set by the United States Department of Energy (DOE).

Energy applications for aligned fibers and scaffold structures produced using the apparatus and methods of the present invention include Li-ion batteries, photovoltaic cells, membrane fuel cells, and dye-sensitized solar cells. Other applications include micro-power to operate personal electronic devices via piezoelectric nanofibers woven into clothing, carrier materials for various catalysts, and photo-catalytic air/water purification.

Using the methods and apparatus of the present invention, aligned fibers may be applied to a substrate comprising a strip of paper, fabric, or tissue. Further heat treatment can be applied to melt the fibers to produce a very strong bond with various substrate types.

Using the methods and apparatus of the present invention, aligned fibers may be arranged in a scaffold like structure and then coated or covered with a flexible bonding material where the combined product is layered on to a damaged surface as a repair or other purpose such as enabling a heating layer when an electric current is applied to the fiber.

Using the methods and apparatus of the present invention, aligned fibers may be arranged in a scaffold structure where the spacing between fibers is adjusted to achieve a substantially specific numerical value to create a filter material having a defined porosity.

The apparatus of the present invention may be used in a portable device movable between user locations to produce and align fiber on a substrate for a specific purpose. The apparatus of the present invention may also be used in a stand-alone device integrated into a laboratory environment to produce and align fiber on a substrate for a plurality of research purposes. The apparatus of the present invention may be used in a stand-alone manufacturing device for producing on a larger scale products incorporating cross-aligned fiber.

The apparatus of the present invention may be used as part of a manufacturing process scaled to produce a relatively high volume of products incorporating aligned fiber. The scaled up manufacturing process may comprise multiple instances of the apparatus of the present invention. The apparatus of the present invention may be configured in a plurality of sizes useable in smaller scale electrospinning machines suitable for low volume production to larger size machines suitable for larger volume production of products incorporating nanofibers. The machines sized in any scale may incorporate multiple segment configurations, and may be reconfigurable.

The apparatus and methods of the present invention may be used to coat a biomedical textile or a wound dressing medical fabric with cross-aligned nanofibers. Single or a plurality of textile or fabric layers may be used to construct a wound dressing. A layered drug delivery dressing can be fabricated using the present methods and apparatus, combining nanofibers formulated for drug release with biomedical textile or other type of wound dressing fabric, and further assembled using components typical of medical dressings, such a matrix, a coagulant, and absorbents.

The apparatus and methods of the present invention enable fabrication of nanofiber scaffolds comprising material exhibiting tunable properties and functions through variation of fiberizable solution compositions. The present invention can be used to electrospin into cross-aligned nanofiber membranes a range of material including, but not limited to, polymer-based, ceramic, metallic, and rare-earth materials. Bioactive particles may be introduced into the solutions forming the fibers or coated onto the fibers. The electrospun fibers may subsequently be part of a final nanocomposite. Non-polymer particles or a second polymer can be mixed into a primary polymer solution and electrospun to form hybrid ultrathin fibers in cross-aligned nanofiber membranes. Nanodispersion of commercial minerals or rare-earth elements into solutions electrospun using the apparatus and methods of the present invention to produce cross-aligned nanofiber membranes may produce specific membrane functionality such as increased thermal resistance, photoluminescence, or the capability to sustain magnetic properties. The apparatus and methods of the present invention can increase the number of functional materials produced and broaden the range of potential applications, including creating advanced multi-functional nanocomposites in which various functions are incorporated for multi-sectorial applications. The present invention may be used in electrospinning nanofiber-reinforced hydrogels, electrospun hydrogels incorporating biological electrospray cells, and electrospun hydrogels including antibacterial and antiviral properties. The hybrid nanostructures made possible by the present invention may be applied in uses such as coatings, packaging, biomedical devices, and other multi-function applications. Biomedical applications enabled by the cross-aligned nanofiber membranes produced by the present invention include, but are not limited to, the engineering of specific soft tissues, such as muscle, nerve, tendon, ligament, skin, and vascular applications. The clinical efficacy of producing these materials is presently impeded by the intrinsic limitations of other methods of electrospinning as disclosed in the prior art. The Traditional electrospinning methods are slow and not amenable to the fabrication of thick scaffolds. These limitations are overcome by the methods and apparatus of the present invention, enabling use of cross-aligned nanofiber polymeric materials for the repair of thin tissues including skin and small blood vessels, fabrication of scaffolds with dimensions necessary for repairing tendons, ligaments, muscle, bone, and potentially large hollow organs.

All types of biodegradable and absorbable polymers may be electrospun into cross-aligned nanofiber membranes using the apparatus and methods of the present invention, including any absorbable and biodegradable polymer that is enzymatically or nonenzymatically decomposed in vivo, yields no toxic decomposition product, and has ability of releasing a drug. Non-limiting examples include any of those selected from polylactic acid, polyglycolic acid, a copolymer of polylactic acid and polyglycolic acid, collagen, gelatin, chitin, chitosan, hyaluronic acid, polyamino acids such as poly-L-glutamic acid and poly-L-lysine, starch, poly-ε-caprolactone, polyethylene succinate, poly-β-hydroxyalkanoate, and the like. These polymers may be used alone or in combination as desired. Further, a biocompatible polymer and a biodegradable polymer may be used in combination to produce cross-aligned nanofiber membranes for a specific a functional purpose.

The apparatus and methods of the present invention enable fabrication of cross-aligned nanofiber membranes incorporating into the fibers immunosuppressants selected from any of tacrolimus (FK506), cyclosporin, sirolimus (rapamycin), azathioprine, mycophenolate mofetil, and analogues thereof; and the antiinflammatory agent is selected from dexamethasone, hydroxycdrtisone, cortisone, desoxycorticosterone, fludrocortisone, betamethasone, prednisolone, prednisone, methylprednisolone, paramethasone, triamcinolone, flumetasone, fluocinolone, fluocinonide, fluprednisolone, halcinonide, flurandrenolide, meprednisone, medrysone, cortisol, 6a.-methylprednisolone, triamcinolone, betamethasone, salicylic acid derivatives, diclofenac, naproxen, sulindac, indomethacin, and analogues thereof.

The apparatus and methods of the present invention enable fabrication of cross-aligned nanofiber membranes incorporating anti-inflammatory agents into the fibers. Examples of the usable anti-inflammatory agents include adrenocortical steroids and non-steroids. Specific non-limiting examples thereof include dexamethasone, hydroxycortisone, cortisone, desoxycorticosterone, fludrocortisone, betamethasone, prednisolone, prednisone, methylprednisolone, paramethasone, triamcinolone, flumetasone, fluocinolone, fluocinonide, fluprednisolone, halcinonide, flurandrenolide, meprednisone, medrysone, cortisol, 6α-methylprednisolone, triamcinolone, betamethasone, salicylic acid derivatives, diclofenac, naproxen, sulindac, indomethacin, and their analogues. In some applications, dexamethasone aid indomethacin may be preferable.

The apparatus and methods of the present invention enable fabrication of cross-aligned nanofiber membranes incorporating hemostatic materials. For example, self-expanding hemostatic polymer may be incorporated into electrospun membranes composed of a superabsorbent polymer and a wicking binder. The hemostatic polymer nanofiber in cross-aligned nanofiber membranes expands rapidly following blood absorption which results in exertion of a direct tamponade effect on the wound surface. Further, concentration of coagulation factors and platelets following absorption of the aqueous phase of blood at the site of bleeding promote clotting. Chitosan solutions may be electrospun using the apparatus and methods of the present invention to provide mucoadhesive components that maintain silica in contact with a wound bed to promote clot formation through adsorption and dehydration, and the advancement of red blood cell bonding. Cross-aligned and radially-aligned nanofiber membranes fabricated through the use of the present invention can provide a temporary skin substitute protecting the wound bed from external contamination, while delivering hemostatic and antibacterial agents, and allowing expulsion of exudates.

The apparatus and methods of the present invention enable fabrication of an absorbable matrix in a single membrane of cross-aligned nanofibers in multiple layers. Each layer can deliver a plurality of compounds including any of a broad spectrum biocide, hemostatic agent, analgesic, regenerative agent, immune modulator, oxygenating agent, and pH stabilizer deep into traumatized wound tissue. The membrane may comprise core-shell nanofiber in alternating fiber layers in a cross-aligned structure that can be used as a "wound packable" membrane, where the nanofibers comprise multiple material compositions in adjacent layers to enable sequenced delivery of an active compound to a trauma wound, with a tunable release profile from the disparate materials comprising the nanofibers.

As reported in the research literature (Mele E. Electrospinning of Essential Oils. *Polymers (Basel)*. 2020; 12(4): 908. Published 2020 Apr. 14), a wide variety of essential oils (EOs) have been electrospun, including at least cinnamon, oregano, peppermint, clove, thyme, lavender, eucalyptus, ginger, tea tree, Manuka, black pepper, and sage. Specific chemical constituents of these essential oils have also been electrospun into fiber. The addition of EOs or their chemical constituents to polymeric solutions is typically accomplished before conducting the electrospinning process, although EOs may be applied as coatings on the fibers as well. The methods and apparatus of the present invention can be used to fabricate nanofiber membranes comprising either cross-aligned or radially aligned fiber or both cross-aligned and radially aligned fiber that deliver EOs as antimicrobial agents to prevent and treat infection in acute, chronic, and trauma wounds, reducing the risk of sepsis. Membranes fabricated using the methods and apparatus of the present invention may also be used as engineered systems for the controlled release of natural EO antimicrobial compounds for use in the field of food preservation.

As a non-limiting example, membranes fabricated using the methods and apparatus of the present invention may be used for the encapsulation and delivery of cinnamon EO as an antimicrobial agent in a topically applied membrane or an absorbable, "wound packable" polymeric fabric (e.g. gauze) for treatment of trauma wounds (e.g. laceration, puncture), or to create active, biodegradable food packaging materials (e.g., membrane, fabric) that can delay food spoilage. Either application serves to inhibit Gram-positive and Gram-negative bacteria. Cinnamon EO may be electrospun in combination with at least the polymers polyvinyl alcohol (PVA), alginate/PVA, polylactic acid (PLA), poly(ethylene oxide) (PEO), and cellulose acetate. The resulting fiber membrane enabled by the present invention may be applied for both food preservation and biomedical uses. Complexes of cinnamon EO and cyclodextrins may be incorporated into VA, PLA, and PEO nanofibers in fabricating the antimicrobial membranes enabled by the methods of the present invention. Cyclodextrins are natural cyclic oligosaccharides characterized by a truncated cone shape exhibiting a hydrophilic external surface and a hydrophobic interior cavity. Cyclodextrins capture EOs in the hydrophobic cavity, which can improve EOs bioavailability and stability. Biodegradable, antimicrobial membranes may be produced by the apparatus and methods of the present invention incorporating into VA, PLA, and PEO nanofibers cinnamon EO and β-cyclodextrin (β-CD).

In another non-limiting example, fiber membranes fabricated using the methods and apparatus of the present invention may comprise absorbable, electrospun polymeric fibers that contain oregano essential oils such as those extracted from *Origanum vulgare* and *Origanum minutiflorum*. The major constituents of oregano EO are carvacrol and thymol, which have been shown to have an inhibitory effect on diverse microorganisms, including Methicillin-resistant *S. aureus* (MRSA), *E. coli, Bacillus subtilis* (*B. subtilis*), and *Saccharomyces cerevisiae*. Oregano EO (and other EOs) acts on the bacteria cell membrane by disrupting its functions. This disruption effect induces loss of cytosolic material and leakage of potassium ions, resulting in eventual cell necrosis. Oregano EO may be used to inactivate biofilms such as those that form in chronic wounds. Biofilms are sessile colonies of bacterial cells that adhere strongly to a wound bed surface. Biofilms are poorly permeable to antibacterial agents and antibiotics, and are a primary inhibitor of wound healing. Applying a polymeric fiber membrane fabricated using the methods of the present invention can provide progressive release of Oregano EO (and other EOs) on a wound bed which may prevent biofilm formation or eradicate formed biofilms.

In another non-limiting example, polymeric fiber membranes fabricated using the methods and apparatus of the present invention may comprise electrospun fibers encapsulating clove EO in polymeric materials including at least PCL, gelatin, CL/gelatine, polyacrylonitrile, alginate/PVA, and polyvinylpyrrolidone. Clove EO has been found effective against *S. aureus, E. coli, B. subtilis, Klebsiella pneumonia, Candida tropicalis*, and *Candida albicans*. CL/gelatine fibres (with a 7:3 PCL:gelatine ratio) containing different concentrations of clove EO (1.5%, 3.0% and 6.0% v/v) have been produced for wound care applications.

In another non-limiting example, polymeric fiber membranes fabricated using the methods and apparatus of the present invention may comprise electrospun fibers encapsulating thyme EO in polymeric material such as poly(vinylpyrrolidone (PVP) and gelatin. PVP/gelatine fibrous mats containing 3% w/w of thyme EO have been found effective against *S. aureus, E. coli, P. aeruginosa*, and *E. faecalis*. Studies have shown that fiber encapsulated EO can maintain the antibacterial activity even when the electrospun fiber is stored at 24 and 37° C., and inhibition activity against *S. aureus* and *E. coli* can remain viable for extend periods of time (e.g., after 8 days of incubation). Among the *Thymus* species, *Thymus vulgaris* L. (commonly known as thyme) is widely used as aromatic and medicinal plant in food, agriculture, pharmaceutical, and cosmetic industries. Thyme EO possesses strong antibacterial and fungicidal activities, being rich in oxygenated monoterpenes and hydrocarbon monoterpenes: thymol, carvacrol, p-cymene and γ-terpinene.

In another non-limiting example, fiber membranes fabricated using the methods and apparatus of the present invention may comprise absorbable electrospun polymeric fibers that deliver stem cells to a wound. Current research literature reports that the healing potency of stem cells enhance burn wound healing; reducing healing time, inflammation levels, scar progression, and on-site fibrosis. Stem cells promote wound healing through angiogenesis, re-epithelialization, granulation, collagen deposition, and inhibition of apoptosis. The fiber membranes fabricated using the methods of the present invention may deliver any of the following stem cells in any combination in any primary layer: Mesenchymal Stem Cells, Bone Marrow Mesenchymal Stem cells, Endometrial gland-derived Mesenchymal cells, Adipose-derived regenerative cells, Stromal Vascular Fraction, Intelligent Acellular Dermal Matrices, Human Platelet Derived Growth Factor-A, Hepatocyte Growth Factor, Vascular Endothelial Growth Factor, Human beta-Defensin 2, Human beta-Defensin 3, Human Wharton's Jelly Stem Cells, Acellular Dermal Matrix, Adipose Tissue-Derived Stem Cells, Leucine-Rich Repeat Containing G-Protein Receptor 6, Polyethylene Glycol-Fibrin, Skin-Derived Keratinocytes, Green Fluorescent Protein, Glycosaminoglycan, Umbilical Cord Blood Derived Mesenchymal Stem Cells. Manolakopoulos, Zacharakis et al, Small Intestinal Submucosa, Prostaglandin E2, Transforming Growth Factor-B1, Human Wharton's Jelly Mesenchymal Stem Cells, Fibroblastic Mesenchymal Stem Cells, Cadaveric Bone Marrow Mesenchynmal Stem Cells, Induced Pluripotent Stem Cell Derived Mesenchymal Stem Cell Line, Fibroblast Growth Factor, Keratinocyte Growth Factor, Induced Pluripotent Stem Cells Derived Microvesicles, Exosomes Derived-Mesenchymal Stem Cells, and Desmoglein 3.

In another non-limiting example, fiber membranes fabricated using the methods and apparatus of the present invention may comprise nanofibers modified with a chromogenic dye to produce a biosensor that can detect bacterial burden present in a wound bed, wound exudate, or bodily fluid. A hemicyanine dye may be incorporated into the shell of an electrospun core-shell nanofiber to form a chromogenic probe with a labile ester linkage that can be enzymatically cleaved by bacterial lipase released from clinically relevant bacterial strains typical of chronic wounds, including at least *Proteus mirabilis, Pseudomonas aeruginosa*, and methicillin-resistant *Staphylococcus aureus* (MRSA). HCy dye loaded into the shell of core-shell polyurethane (PU) nanofibers localizes at the surface of the shell during electrospinning, which improves accessibility of the dye to lipase. The PU fiber is degraded by the lipase exposing the dye, where the dye is cleaved by the lipase producing a visible color change. By incorporating polyvinylpyrrolidone (PVP) dopant in the shell, the sensitivity can be boosted to enable detection of bacteria at clinically relevant concentrations after limited time (e.g. 2 hours) exposure, where sensitivity is in the range $2.5 \times 10^5$ CFU/cm$^2$ *P. aeruginosa* and $1.0 \times 10^6$ CFU/cm$^2$ MRSA. Introduction of PVP in the shell can also boost the degree of hydrolysis of the chromogenic probe by a factor of 1.2× after 3 h exposure to a low concentration of *P. aeruginosa* ($10^5$ CFU/cm$^2$). PVP has be found to improve the discernibility of the color change at high bacterial concentrations. Cross-alignment of fibers in one fiber layer relative to fibers in adjacent layers presents a well-structured matrix of fibers that increases fiber surface area exposure in a wound bed in contrast to the random orientation of fibers comprising fibrous mats produced by traditional electrospinning. Uniformity of fiber alignment in each layer combined with relative uniformity of cross-alignment angle of fibers in adjacent fiber layers produces porosity in the membrane that encourages fiber exposure to secreted lipase in all layers. A more uniform exposure of fibers to lipase may produce a more robust response and color change correlating with degree of bacterial colonization in a wound. The same response mechanism recited above can expose an antimicrobial agent immobilized in the core of a core-shell nanofiber, and combined with detection of clinically relevant bacteria and corresponding visual color change, produce a theranostic membrane that detects rising bacterial colonization in a wound, provides a visual indicator, and progressive releases the antimicrobial agent over an extended time period to therapeutically treat bacterial infection.

Referring to FIG. 25, a non-limiting diagram is shown of a prototype of the segmented collector of the present invention installed in a commercially available laboratory scale electrospinning machine.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Further, it is to be understood that the invention may be utilized and practiced other than as specifically described. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A wound dressing comprising:
   any of a medical fabric, a film, or a porous material;
   a fiber membrane, comprising electrospun fiberizeable material in at least three adjacent layers of nanofibers, each layer comprising a plurality of aligned nanofibers oriented at oblique angles relative to nanofibers in adjacent layers, said plurality of aligned nanofibers in each layer extending from a first membrane edge to a second membrane edge,
   wherein a plurality of aligned nanofibers in each layer cross a plurality of aligned nanofibers in adjacent layers at a plurality of distinct points of intersection, forming a crossing at each distinct point of intersection consisting of three crossing nanofibers extending directionally as six radials from each of said distinct points of intersection,
   wherein relative cross-alignment angles between said six radials at each distinct point of intersection are in the range of 50 to 70 degrees, and said relative cross-alignment angles of said aligned nanofibers and spacing between said aligned nanofibers each have a specific average numerical value in said membrane and comprise a structure having porosity required for exudate flow from a wound, and
   wherein said aligned nanofibers in each said layer comprise at least one of solid, hollow, or core-shell fiber.

2. The wound dressing of claim 1, further comprising any combination of said fiber membrane, film, medical fabric, or porous material.

3. The wound dressing of claim 1, further comprising any of an antimicrobial agent, hemostatic agent, analgesic agent, regenerative agent, immune modulator, oxygenating agent, and pH stabilizer.

4. The wound dressing of claim 1, wherein said nanofibers comprise any one or combination of poly (lactic-co-glycolic acid) (PLGA), polyvinylpyrrolidone (PVP), poly(ethyleneoxide) (PEO), polyurethane (PU), PVP/cyclodextrin, polyvinyl alcohol (PVA), polycaprolactone (PCL), cellulose, PVP/ethyl cellulose, PVP/zein, cellulose acetate, hydroxypropyl methylcellulose (HPMC), and analogues thereof.

5. The wound dressing of claim 1, wherein said nanofibers comprise an absorbable and biodegradable polymer that can be enzymatically or nonenzymatically decomposed, yields no toxic decomposition product, and has ability of releasing a drug.

6. The wound dressing of claim 1, wherein said nanofibers further comprise a polymeric material and a chromogenic agent responsive to enzymatic activity.

7. The wound dressing of claim 6, wherein said chromogenic agent is a dye presenting a color change response to said enzymatic activity produced by pathogens present on human skin, in a wound bed, in wound exudate, or in bodily fluid.

8. The wound dressing of claim 7, wherein said enzymatic activity produces lipase.

9. The wound dressing of claim 7, wherein said pathogens include at least *Proteus mirabilis, Pseudomonas aeruginosa*, and methicillin-resistant *Staphylococcus aureus* (MRSA).

10. A wound dressing, comprising:
   any of a medical fabric, a film, and a porous material, or any combination thereof;
   electrospun fiberizeable material in at least three adjacent layers of nanofibers, each layer comprising a plurality of aligned nanofibers oriented at oblique angles relative to nanofibers in adjacent layers, said plurality of aligned nanofibers in each layer extending from a first membrane edge to a second membrane edge,
wherein a plurality of aligned nanofibers in each layer cross a plurality of aligned nanofibers in adjacent layers at a plurality of distinct points of intersection, forming a crossing at each distinct point of intersection consisting of three crossing nanofibers extending directionally as six radials from each of said distinct points of intersection,
wherein relative cross-alignment angles between said six radials at each distinct point of intersection are in the range of 50 to 70 degrees, and said relative cross-alignment angles of said aligned nanofibers and spacing between said aligned nanofibers each have a specific average numerical value in said membrane,
wherein said nanofibers further comprise a polymeric material and a chromogenic agent responsive to enzymatic activity, and
wherein said nanofibers further comprise an absorbable and biodegradable polymer that can be enzymatically or nonenzymatically decomposed, yields no toxic decomposition product, and has ability of releasing a drug.

11. The wound dressing of claim 10, wherein said chromogenic agent is a dye presenting a color change response to said enzymatic activity produced by pathogens present on human skin, in a wound bed, in wound exudate, or in bodily fluid.

12. The wound dressing of claim 11, wherein said enzymatic activity produces lipase.

13. The wound dressing of claim 11, wherein said pathogens include at least *Proteus mirabilis, Pseudomonas aeruginosa*, and methicillin-resistant *Staphylococcus aureus* (MRSA).

14. The wound dressing of claim 11, wherein said aligned nanofibers in each said layer comprise at least one of solid, hollow, or core-shell fiber.

15. The wound dressing of claim 10, wherein said nanofibers comprise any one or combination of poly (lactic-co-glycolic acid) (PLGA), polyvinylpyrrolidone (PVP), poly (ethyleneoxide) (PEO), polyurethane (PU), PVP/cyclodextrin, polyvinyl alcohol (PVA), polycaprolactone (PCL), cellulose, PVP/ethyl cellulose, PVP/zein, cellulose acetate, hydroxypropyl methylcellulose (HPMC), and analogues thereof.

16. The wound dressing of claim 11, wherein said medical fabric is a woven or non-woven biomedical textile comprising organic or synthetic polymers.

17. The wound dressing of claim 11, wherein said wound bed comprises any of full and partial thickness burns, ulcerated skin, punctured skin, and traumatized tissue.

18. The wound dressing of claim 11, wherein said medical fabric and said porous material are absorbent.

19. The wound dressing of claim 18, wherein said enzymatic activity produces lipase.

20. The wound dressing of claim 19, wherein said pathogens include at least *Proteus mirabilis, Pseudomonas aeruginosa*, and methicillin-resistant *Staphylococcus aureus* (MRSA).

* * * * *